US012604866B2

(12) United States Patent
Sun et al.

(10) Patent No.: US 12,604,866 B2
(45) Date of Patent: Apr. 21, 2026

(54) FULL-AUTOMATIC PET CLEANING MACHINE, AND CONTROL METHOD AND CONTROL SYSTEM OF THE FULL-AUTOMATIC PET CLEANING MACHINE

(71) Applicant: Allviews Technology LLC, Tempe, AZ (US)

(72) Inventors: Hongxia Sun, Tempe, AZ (US); Sean Langley, Phoenix, AZ (US); Yaxin Peng, Chandler, AZ (US); Mingxuan Wang, Phoenix, AZ (US); Yaqian Peng, Chandler, AZ (US); Jing Zhang, Calgary (CA)

(73) Assignee: Allviews Technology LLC

( * ) Notice: Subject to any disclaimer, the term of this patent is extended or adjusted under 35 U.S.C. 154(b) by 0 days.

(21) Appl. No.: 18/829,372

(22) Filed: Sep. 10, 2024

(65) Prior Publication Data

US 2026/0020541 A1     Jan. 22, 2026

(30) Foreign Application Priority Data

Jul. 16, 2024     (CN) .......................... 202410955195.9

(51) Int. Cl.
    *A01K 13/00*        (2006.01)
    *A46B 9/02*         (2006.01)
    (Continued)

(52) U.S. Cl.
    CPC ............ *A01K 13/001* (2013.01); *A46B 9/026* (2013.01); *A46B 13/003* (2013.01); *A46B 13/04* (2013.01);
    (Continued)

(58) Field of Classification Search
    CPC ........... A01K 13/01; A61L 2/10; A46B 13/02; A46B 13/04; A46B 15/0004; A46B 15/0012; A46B 9/026
    See application file for complete search history.

(56) References Cited

U.S. PATENT DOCUMENTS 11,033,001 B2 * 6/2021 Zhang .................. A01K 13/001
11,375,694 B2 * 7/2022 Kim ..................... A01K 13/001
(Continued)

FOREIGN PATENT DOCUMENTS

CN         106342716 A  *  1/2017  ........... A01K 13/001
CN         111837997 A  *  10/2020  ........... A01K 13/001
(Continued)

OTHER PUBLICATIONS

A Front Cleaning Device for Breeding Meat Pig Slaughtering (Year: 2020).*

(Continued)

*Primary Examiner* — Christopher D Hutchens
*Assistant Examiner* — Nevena Aleksic
(74) *Attorney, Agent, or Firm* — Bayramoglu Law Offices LLC

(57) ABSTRACT

The provided are a full-automatic pet cleaning machine, and a control method and a control system of the full-automatic pet cleaning machine. The full-automatic pet cleaning machine includes a bathing mechanism and a drying mechanism. The bathing mechanism is used to clean a pet, and the drying mechanism is used to dry hair of the pet. This full-automatic pet cleaning machine can complete the washing, rinsing, drying and disinfection processes of the pet automatically, ensuring the cleaning quality and the comfort and safety of the pet.

11 Claims, 12 Drawing Sheets

(51) Int. Cl.

| | |
|---|---|
| *A46B 13/00* | (2006.01) |
| *A46B 13/04* | (2006.01) |
| *A46B 15/00* | (2006.01) |
| *A46D 1/00* | (2006.01) |
| *A61L 2/10* | (2006.01) |
| *A61L 2/24* | (2006.01) |
| *A61L 2/26* | (2006.01) |

(52) U.S. Cl.
CPC ........ *A46B 15/0012* (2013.01); *A46B 15/003* (2013.01); *A46D 1/0246* (2013.01); *A61L 2/10* (2013.01); *A61L 2/24* (2013.01); *A61L 2/26* (2013.01); *A46B 2200/1093* (2013.01); *A61L 2202/11* (2013.01); *A61L 2202/14* (2013.01); *A61L 2202/17* (2013.01)

(56) References Cited

U.S. PATENT DOCUMENTS

| | | | |
|---|---|---|---|
| 11,547,087 B2 * | 1/2023 | Munneke ............. | A01K 13/004 |
| 12,279,593 B2 * | 4/2025 | Nachtigall-Fournier ................... | A01K 13/003 |
| 2015/0100037 A1 * | 4/2015 | Allsup ................. | A01K 13/002 |
| | | | 119/51.01 |

FOREIGN PATENT DOCUMENTS

| | | | | | |
|---|---|---|---|---|---|
| CN | 112841064 A | * | 5/2021 | ........... | A01K 13/001 |
| CN | 115250944 A | * | 11/2022 | ........... | A01K 13/002 |
| CN | 115475084 A | * | 12/2022 | ............. | F04D 25/08 |

OTHER PUBLICATIONS

A Hair Cleaning Device for Breeding Livestock (Year: 2017).*
A Beef Cattle Massager for Automatically Brushing Hair (Year: 2022).*
A Cattle Body Surface Cleaning Device for Livestock Breeding (Year: 2021).*
An Automatic Cleaning Device for Cleaning Cattle Body (Year: 2022).*

* cited by examiner

FULL-AUTOMATIC PET CLEANING MACHINE, AND CONTROL METHOD AND CONTROL SYSTEM OF THE FULL-AUTOMATIC PET CLEANING MACHINE

CROSS-REFERENCE TO THE RELATED APPLICATIONS

This application is based upon and claims priority to Chinese Patent Application No. 202410955195.9, filed on Jul. 16, 2024, the entire contents of which are incorporated herein by reference.

TECHNICAL FIELD

The present invention relates to the technical field of full-automatic pet cleaning machines for pet care, and in particular, to a full-automatic pet cleaning machine, and a control method and a control system of the full-automatic pet cleaning machine.

BACKGROUND

Pet cleaning has always been a task to which pet owners pay more attention. Most families use ordinary showers or bathtubs to clean the pets. As people pay more and more attention to pets, various automatic pet cleaning machines for automatically cleaning pets have emerged.

The conventional pet cleaning method relies heavily on manual operation, which is not only labor-intensive, but also difficult to ensure uniformity and thoroughness of cleaning. In addition, pets may feel uncomfortable due to uneven techniques or inappropriate water temperature in conventional cleaning method. However, there is no full-automatic pet cleaning machine in the prior art that can automatically complete the cleaning process and ensure the safety and comfort of pets.

Therefore, how to provide a full-automatic pet cleaning machine, and a control method and a control system of the full-automatic pet cleaning machine that can solve the above problems is an issue required to be resolved urgently by those skilled in the art.

SUMMARY

In view of this, the present invention provides a full-automatic pet cleaning machine, and a control method and a control system of the full-automatic pet cleaning machine, which are used to solve the technical problems in the prior art.

To achieve the above objective, the present invention provides the following technical solutions.

A full-automatic pet cleaning machine comprises: a bathing mechanism and a drying mechanism, wherein the bathing mechanism is used to clean a pet, and the drying mechanism is used to dry hair of the pet;

the bathing mechanism comprises: a water outlet mechanism and a cleaning terminal mechanism connected to the water outlet mechanism;

the cleaning terminal mechanism comprises: a rack, a horizontal lead screw, a vertical lead screw, a vertical slide rail, a self-rotating motor, a Y-direction servo motor, a Z-direction servo motor and roller brushes;

two groups of roller brushes are symmetrically arranged along two moving seats of the rack, each group of roller brushes comprises two roller brushes, each roller brush is rotatably mounted on a corresponding mounting seat, one end of each roller brush is provided with one self-rotating motor, an end part of an output shaft of the self-rotating motor is provided with a corresponding pressure sensor, and the self-rotating motor controls self-rotation motion of the corresponding roller brush based on feedback information of the corresponding pressure sensor;

one side of each group of roller brushes is connected to the vertical lead screw, the other side of each group of roller brushes is connected to the vertical slide rail, one end of the vertical lead screw is provided with the Z-direction servo motor, an end part of an output shaft of the Z-direction servo motor is provided with a corresponding pressure sensor, and the Z-direction servo motor controls the vertical lead screw to rotate based on feedback information of the corresponding pressure sensor to drive the roller brush to move vertically; and the horizontal lead screw is rotatably mounted at a top of the rack, two ends of the horizontal lead screw are in threaded connection with the two moving seats respectively, an end part of an output shaft of the Y-direction servo motor is provided with a corresponding pressure sensor, and the Y-direction servo motor controls the horizontal lead screw to rotate based on feedback information of the corresponding pressure sensor to drive the roller brush to move horizontally.

The roller brush comprises:

a roller, antenna fixing blocks, antennas and a water-air interface;

the antenna fixing blocks are circumferentially arranged on an outer wall of the roller and are semicircular cylinders, a hollow support cylinder is formed by the two antenna fixing blocks, and the water-air interface is formed in the support cylinder and is used to pass water and gas; and the antennas are hollow conical cylinders that are up-and-down communicated, each of the antennas is fixed in a mounting groove of the antenna fixing block by an end step structure and forms a hollow connection with the support cylinder, and the antenna is used to spray water or detergent foam in a cleaning stage and to blow hot air in a drying stage.

The roller brush is connected to a fixing block, the fixing block is connected to a connecting block, the connecting block is provided with reverse threads engaged with threads of the vertical lead screw, and the connecting block is driven by the Z-direction servo motor to move vertically.

The self-rotating motor controlling self-rotation motion of the corresponding roller brush based on feedback information of the corresponding pressure sensor comprises:

$$\omega_i \begin{cases} 0.5 \cdot \omega_{max}, & P_i < P_{low} \\ \omega_{max}, & P_{low} \le P_i \le P_{mid} \\ \omega_{max}\left(1 - \dfrac{P_i - P_{mid}}{P_{high} - P_{mid}}\right), & P_{mid} \le P_i \le P_{high} \\ 0, & P_i > P_{high} \end{cases}$$

wherein $\omega_i$ represents a motion parameter value controlled by an $i^{th}$ self-rotating motor, $P_i$ represents information of an $i^{th}$ pressure sensor, $P_{low}$ represents a set low pressure value, $P_{mid}$ represents a set medium pressure value, and $P_{high}$ represents a set high pressure value.

The Z-direction servo motor controlling the vertical lead screw to rotate based on feedback information of the corresponding pressure sensor to drive the roller brush to move vertically comprises:

$$\omega_j \begin{cases} A, & P_j < P_{j,low} \\ 0, & P_{j,low} \leq P_j \leq P_{j,high} \\ -A, & P_j > P_{j,high} \end{cases}$$

wherein $\omega_j$ represents a rotation speed parameter value of the Z-direction servo motor at the position j, the motor rotates forwardly when $\omega_j$ is a positive number, two roller brushes connected to the vertical lead screw move in a vertical direction close to each other, the motor rotates reversely when $\omega_j$ is a negative number, two roller brushes connected to the vertical lead screw move in a vertical direction away from each other, and A is a constant and represents a normal rotation speed value of the Z-direction servo motor. $P_j$ represents a pressure value of the pressure sensor of the Z-direction servo motor at j, $P_{j,low}$ represents a low pressure value set at j, and $P_{j,high}$ represents a high pressure value set at j.

The Y-direction servo motor controlling the horizontal lead screw to rotate based on feedback information of the corresponding pressure sensor to drive the roller brush to move horizontally comprises:

$$\omega_k \begin{cases} B, & P_k < P_{k,mid} \\ 0, & P_{k,mid} \leq P_k \leq P_{k,high} \\ -B, & P_k > P_{k,high} \end{cases}$$

wherein $\omega_k$ represents a rotation speed parameter value of the Y-direction servo motor at k, the motor rotates forwardly when $\omega_k$ is a positive number, the roller brushes of the two moving seats connected to the horizontal lead screw move towards a horizontal direction close to each other, the motor rotates reversely when $\omega_k$ is a negative number, the roller brushes of the two moving seats connected to the horizontal lead screw move towards a horizontal direction away from each other, B is a constant and represents a first rotation speed value of the Y-direction servo motor, $P_k$ represents an instantaneous pressure value of the pressure sensor at k where the Y-direction servo motor is positioned, $P_{k,mid}$ represents a medium pressure value set at k, and $P_{k,high}$ represents a high pressure value set at k.

A side panel of the rack is provided with an infrared photoelectric sensor, which monitors position information of the pet and feeds back the information to the Y-direction servo motor, and the Y-direction servo motor controlling the horizontal lead screw to rotate based on feedback information of the corresponding pressure sensor or the feedback information of the infrared photoelectric sensor to drive the roller brush to move horizontally comprises:

$$\omega_k \begin{cases} C, & d_k < d_{high} \\ 0, & d_{mid} \leq d_k \leq P_{high} \\ -C, & d_k > d_{mid} \end{cases}$$

wherein $\omega_k$ represents a rotation speed parameter value of the Y-direction servo motor at k, the motor rotates forwardly when $\omega_k$ is a positive number, the roller brushes of the two moving seats connected to the horizontal lead screw move towards a horizontal direction close to each other, the motor rotates reversely when $\omega_k$ is a negative number, the roller brushes of the two moving seats connected to the horizontal lead screw move towards a horizontal direction away from each other, C is a constant and represents a second rotation speed value of the Y-direction servo motor, $d_k$ represents an instantaneous distance value of the infrared photoelectric sensor of the Y-direction servo motor at k, $d_{mid}$ represents an upper limit value of a safe distance set at k, and $d_{high}$ represents a maximum distance value set at k.

The control program of the Y-direction servo motor simultaneously receives 2 independent feedback information, one is the feedback information of the pressure sensors and the other is the feedback information of the infrared photoelectric sensors. The priority statement is as follows:

1, whichever is triggered first is the priority, which is a "redundancy" or "insurance" for safety considerations;

2. the two sensors are controlled normally by the main program when there is no abnormality, the two sensors are just auxiliary "insurance", and only when there is danger, one sensor that is triggered first is the top priority; and 3. when there is no abnormality, B and C are both 0, the state is motion maintenance, there is no feedback, and the maintained motor rotating speed is the set value of the main program, which works normally.

The control program of the Y-direction servo motor is controlled by the main control program and simultaneously receives feedback information of the pressure sensor and the infrared photoelectric sensor, and the instruction for controlling the rotation of the horizontal lead screw is executed based on the priority of the instruction corresponding to the feedback information.

The Y-direction servo motor controls the horizontal lead screw to rotate based on the feedback information of the corresponding pressure sensor or infrared photoelectric sensor, and the two sensors are in an "OR" relationship. Whichever is triggered first is the priority, and two sensors can affect the Y-direction servo motor, which is a "redundancy" or "insurance" for safety considerations.

The control program of the Y-direction servo motor is controlled by the main control program and simultaneously receives feedback information of the pressure sensor and the infrared photoelectric sensor, and the instruction for controlling the rotation of the horizontal lead screw is executed based on the priority of the instruction corresponding to the feedback information. A control instruction for moving the roller brushes away from each other is higher than an instruction for keeping the roller brushes in position, and the position keeping instruction is higher than a control instruction for moving the rollers closer to each other. Meanwhile, a first rotation speed B of the Y-direction servo motor has a higher priority than a second rotation speed C.

Two adjacent surfaces of the two moving seats of the rack are respectively provided with a bathing inlet and a bathing outlet, and an inner side of the top of the rack is provided with an ultraviolet lamp through which disinfection is performed.

The water outlet mechanism comprises: a water storage device, a heating part, a water mist spray head, a storage box, a pressure pump, a peristaltic pump, a pipeline assembly and a mesh plate;

the water storage device is used to store water for cleaning;

the water stored in the water storage device is heated by the heating part and kept at a certain temperature;

a plurality of the water mist spray heads are arranged on inner side walls, an inner lower wall and an inner top wall of the rack, and the water for cleaning is converted into high-pressure fine water mist for cleaning the pet by the water mist spray heads to rinse the body of the pet without any dead angle;

the storage box is connected to the water storage device by the pipeline assembly, the peristaltic pump is arranged at an outlet end of the storage box, and a cleaning liquid (shower gel and/or deodorant) placed in the storage box flows out through the peristaltic pump and merges with the water in the water storage device at a connection of the pipeline assembly to enter the pipeline to produce a mixed liquid;

the mixed liquid or the water for cleaning, after being pressurized by the pressure pump, flows into the roller brush through the pipeline assembly to spray the mist liquid; and the mesh plate discharges cleaning wastewater.

The drying mechanism comprises: an electric heating element, an inlet fan and an air supply fan;

after passing through the inlet fan, room temperature air is heated by the electric heating element and then blown towards the inside of the rack by the air supply fan, and the hair of the pet is dried.

The drying mechanism further comprises: a temperature sensor, and a drying temperature is controlled based on feedback information of the temperature sensor, wherein a control logic is set up as follows:

$$\omega(T)\begin{cases}\omega_{max}, & T \leq T_{high}\\\omega_{max}\left(1 - \dfrac{T - T_{high}}{T_{safe} - T_{high}}\right), & T_{mid} \leq T \leq T_{safe}\\0, & T \geq T_{safe}\end{cases}$$

wherein $\omega(T)$ represents a rotation speed parameter value of a servo motor when the temperature sensor displays temperature T, T represents a displayed temperature value of the temperature sensor, $T_{safe}$ represents an upper limit of a safety temperature inside equipment, and $T_{high}$ represents a high temperature mark value inside the equipment.

If the pressure sensor signal, the infrared photoelectric sensor and the temperature sensor signal are simultaneously generated, the temperature sensor instruction is executed with the highest priority, that is, the rotation speed of the self-rotating motor is 0, the Y-direction motor moves away, the Z-direction motor moves away, and the electric heating element is powered off.

A control method of a full-automatic pet cleaning machine that is the full-automatic pet cleaning machine according to any one of above aspects comprises the following steps:

step I: adjusting parameters based on a pet type, a pet physique and a hair type;

step II: opening a bathing door, and closing the bathing door after a pet enters the cleaning machine;

step III: performing warm water spraying on four sides by a heating system and the pressure pump to moisten the hair and the skin of the pet; controlling a shower gel to be released from the storage box, delivered to the water mist spray head through the pipeline and then sprayed after mixing with the water for cleaning; controlling the self-rotation of the roller brush, the horizontal motion of the roller brush, and the vertical motion of the roller brush to scrub the pet;

step IV: closing a switch of the storage box for placing the shower gel, continuously spraying clear water to remove shower gel residues, and scrubbing the pet through the self-rotation of the roller brush, the horizontal motion of the roller brush, and the vertical motion of the roller brush;

step V: returning the roller brush to an original position, and rinsing the pet by using clear water through the water mist spray head;

step VI: drying the hair of the pet through a hot air blowing dry part;

step VII: after the cleaning is completed, opening the bathroom door; and step VIII: sterilizing with the ultraviolet lamp, and releasing deodorant for deodorization.

A control system of a full-automatic pet cleaning machine that is the full-automatic pet cleaning machine according to any one of above aspects comprises:

a main control module, a servo-driven control module, a water system control module and a drying control module;

the main control module is connected to the servo-driven control module, the water system control module and the drying control module and is configured to perform control and program management on the servo motor control module, the water system control module and the drying control module;

the main control module sends a control instruction to the servo-driven control module, and the servo-driven control module controls operations of the self-rotating motor, the Y-direction servo motor and the Z-direction servo motor based on the control instruction;

the water system control module controls storage, distribution and release of the cleaning liquid placed in the storage box, and ensures that the cleaning liquid is used reasonably based on the size and hair type of the pet; and the drying control module controls a drying temperature of the drying mechanism, and ensures the drying effect and the safety of the pet during the drying.

The water system control module comprises: a first cleaning unit, a second cleaning unit and a third cleaning unit;

the first cleaning unit controls the heating system and the pressure pump to spray warm water on four sides to moisten the hair and skin of the pet; controls the shower gel to be released from the storage box, delivered to the water mist spray head through the pipeline and then sprayed after mixing with the water for cleaning; and controls the self-rotation of the roller brush, the horizontal motion of the roller brush, and the vertical motion of the roller brush to scrub the pet;

the second cleaning unit controls to close a switch of a storage box for placing a shower gel, continuously sprays clear water to remove shower gel residues, controls the self-rotation of the roller brush, the horizontal motion of the roller brush and the vertical motion of the roller brush to scrub the pet; and the third cleaning unit controls the roller brush to return to the original position, and rinses the pet by using clear water through the water mist spray head.

It can be known from the above technical solutions that, compared with the prior art, the present invention provides a full-automatic pet cleaning machine, and a control method and a control system of the full-automatic pet cleaning machine. This full-automatic pet cleaning machine can complete the washing, rinsing, drying and disinfection processes of the pet automatically, ensuring the cleaning quality and the comfort and safety of the pet. Specific beneficial effects:

(1) The arranged servo motor can accurately adjust the rotation and movement of the rollers to achieve efficient cleaning and contour massage of the body of the pet.

(2) The arranged roller brushes can adjust the contact strength with the body of the pet to improve the cleaning effect.

(3) Through the arrangement of a plurality of sensors, the states of the pet and equipment can be monitored in real time, and the information can be automatically fed back to adjust the motor movement to ensure the cleaning and drying effect.

(4) The top of the rack is provided with a storage box loaded with a shower gel and a disinfectant, and the storage box is connected to the misting spray head through the pipeline assembly.

(5) The water storage device, the heating part and the pressure pump thereof are provided to ensure that the spraying water has a certain impact force, thereby cleaning the pet more effectively.

BRIEF DESCRIPTION OF THE DRAWINGS

To more clearly illustrate the technical solutions in the embodiments of the present invention or in the prior art, the accompanying drawings required to be used in the description of the embodiments or the prior art are briefly introduced below. It is obvious that the accompanying drawings in the description below are merely embodiments of the present invention, and those of ordinary skill in the art can obtain other drawings according to the accompanying drawings provided without creative efforts.

In FIGS. 1 to 12, 1: storage box; 2: Y-direction servo motor; 3: roller brush; 4: electric heating element; 5: rack; 6: water storage device; 7: pressure pump; 8: inlet fan; 9: air supply fan; 10: pipe assembly; 11: mesh plate; 12: water collecting tray, 13: top plate, 14: second pressure sensor, 15: third pressure sensor; 16: peristaltic pump;

20: first belt pulley mechanism; 21: horizontal lead screw; 22: Z-direction servo motor; 23: second belt pulley mechanism; 24: self-rotating motor; 25: vertical lead screw; 26: first pressure sensor; 27: infrared photoelectric sensor; 28: temperature sensor; 29: connecting block;

30: movable block; 31: fixing block; 32: side panel; 33: lead screw fixing block; 34: bottom fixing block; 35: horizontal slide rail; 36: vertical slide rail; 37: water pipe joint; 39: slider fixing block;

40: top spray head; 41: water mist spray head; 45: top fixing block; 46: top connecting block; 47: bottom connecting block;

51: slider connecting block;

62: water-air interface; 63: roller; 66: antenna fixing blocks; 65: antenna;

102: room temperature air; 103: outlet fan; and 104: closed space.

DETAILED DESCRIPTION OF THE EMBODIMENTS

The following clearly and completely describes the technical solutions in the embodiments of the present invention with reference to drawings in the embodiments of the present invention. It is clear that the described embodiments are merely a part rather than all of the embodiments of the present invention. Based on the embodiments in the present invention, all other embodiments obtained by those of ordinary skill in the art without making any creative effort fall in the protection scope of the present invention.

Figure 1:
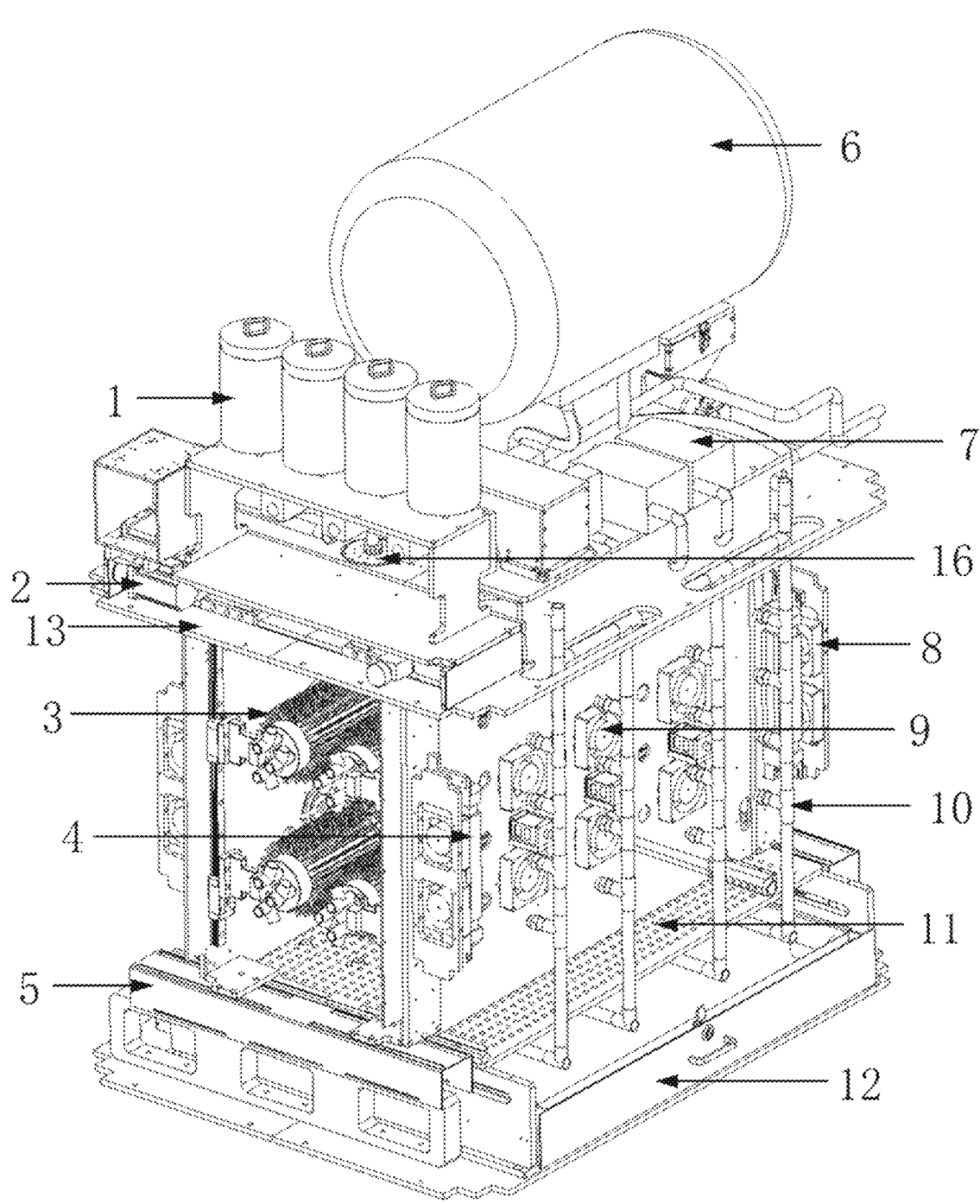
FIG. 1 is a diagram of an internal main structure of pet cleaning equipment.
Figure 2:
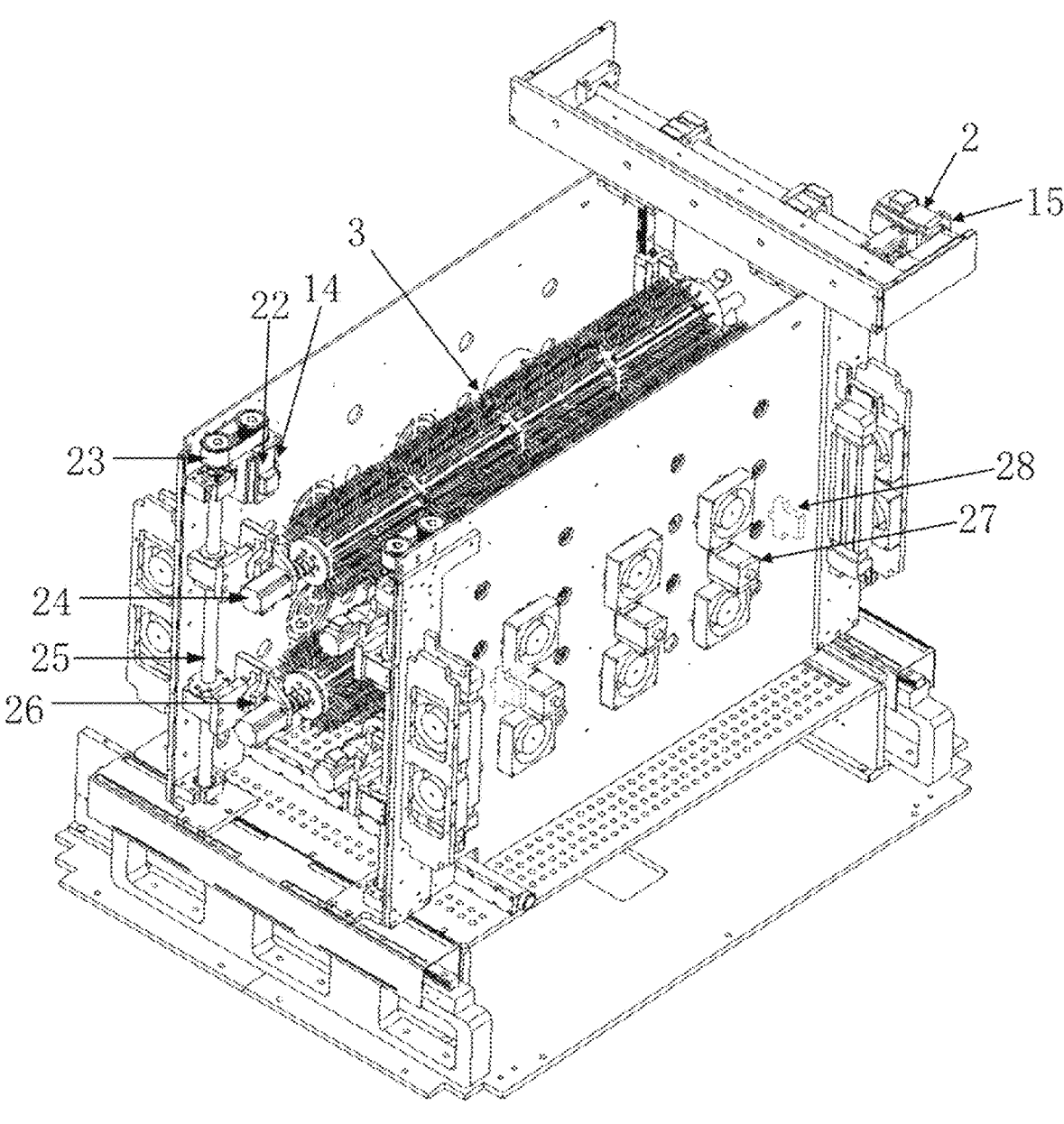
FIG. 2 is a partial schematic diagram of a motor roller inside the equipment.

Referring to FIGS. 1 to 4, an embodiment of the present invention provides a full-automatic pet cleaning machine, which comprises:

a bathing mechanism and a drying mechanism, wherein the bathing mechanism is used to clean a pet, and the drying mechanism is used to dry hair of the pet. An internal main structure of the pet cleaning equipment is shown in FIG. 1.

The bathing mechanism comprises: a water outlet mechanism and a cleaning terminal mechanism connected to the water outlet mechanism;

the cleaning terminal mechanism comprises: a rack 5, a horizontal lead screw 21, a vertical lead screw 25, a self-rotating motor, a Y-direction servo motor 2, a Z-direction servo motor 22 and roller brushes 3;

two groups of roller brushes 3 are symmetrically arranged along two moving seats of the rack 5, each group of roller brushes 3 comprises two roller brushes, each roller brush 3 is rotatably mounted on a corresponding mounting seat, one end of each roller brush 3 is provided with one self-rotating motor, an end part of an output shaft of the self-rotating motor is provided with a corresponding first pressure sensor 26, and the self-rotating motor controls self-rotation motion of the corresponding roller brush 3 based on feedback information of the corresponding first pressure sensor 26;

one side of each group of roller brushes 3 is connected to the vertical lead screw 25, the other side of each group of roller brushes 3 is connected to a vertical slide rail 36 through a slider fixing block 39, one end of the vertical lead screw 25 is provided with a Z-direction servo motor 22, the other end of the vertical lead screw is connected to a lead screw fixing block 33, an end part of an output shaft of the Z-direction servo motor 22 is provided with a corresponding second pressure sensor 14, and the Z-direction servo motor 22 controls the vertical lead screw 25 to rotate based on feedback information of the corresponding second pressure sensor 14 to drive the roller brush 3 to vertically move;

the horizontal lead screw 21 is rotatably mounted at a top of the rack 5, two ends of the horizontal lead screw 21 are in threaded connection with the two moving seats respectively, an end part of an output shaft of the Y-direction servo motor 2 is provided with a corresponding third pressure sensor 15, and the Y-direction servo motor 2 controls the horizontal lead screw 21 to rotate based on feedback information of the corresponding pressure sensor 15 to drive the roller brush 3 to move horizontally.

Specifically, the roller brushes 3 are respectively positioned at the moving seats at left and right sides in the rack 5, 2 groups of roller brushes are provided at each of the left and right sides, and the 2 groups of roller brushes 3 at each side are arranged in parallel in an upper and lower position and perpendicular to the Z direction and the Y direction along a side panel 32. A front end of the roller brush 3 is connected to the vertical lead screw 25 by a fixing block 31 and a connecting block 29, and a rear end of the roller brush 3 is connected to a vertical slide rail at a rear end of the rack 5 by a slider fixing block 39 and a movable block 30. The vertical movement of the roller brush 3 is along a vertical motion track, and the parallel movement of the roller brush 3 is along a horizontal motion track by the vertical lead screw 25 and a corresponding vertical slide rail.

More specifically, the horizontal lead screw 21 is arranged at a horizontal position above the front end of the rack 5, a first belt pulley mechanism 20 is arranged at a left end of the horizontal lead screw 21, and a belt pulley and a transmission belt included in the first belt pulley mechanism 20 are connected to the Y-direction servo motor 2. A horizontal slide rail parallel to the upper horizontal lead screw 21 is arranged at a lower position of the front end of the rack 5 corresponding to the horizontal lead screw 21, and forms a horizontal motion track at the front end of the roller brush 3 together with the horizontal lead screw 21. At the rear end of the rack 5, the horizontal lead screw 21 and the slide rail parallel to the front end of the rack 5 are respectively provided with corresponding slide rails, and form a horizontal motion track at the rear end of the roller brush 3.

The vertical lead screws 25 are arranged at the vertical positions of the front ends of the side panels 32 at left and right sides of the rack 5, and the second belt pulley mechanisms 23 including the belt pulleys and transmission belts are arranged at the lateral positions of the upper ends of the vertical lead screws 25 to be connected to the Z-direction servo motors 22, and the second belt pulley mechanisms 23 and the Z-direction servo motors 22 are fixed on the side panels 32 of the rack 5. At the left and right sides of the rear end of the rack 5, the vertical lead screws 25 parallel to the left and right sides of the front end of the rack 5 are provided with corresponding vertical slide rails 36, which form a vertical motion track at the front and rear ends of the roller brush 3 together with the vertical lead screws 25. The top of the upper end of the vertical lead screw 25 is connected to the horizontal lead screw 21 by the fixing block 31 and the connecting block 29 which are connected to the upper part of the side panel 32, the lower end of the vertical lead screw 25 is connected to the horizontal slide rail at the lower end by the fixing block 31 and the movable block 30, and the upper end and the lower end of the vertical slide rail at the left side and the right side of the rear end are respectively connected to the horizontal slide rail at the rear end by the fixing block 31 and the movable block 30.

The self-rotating motor, the Y-direction servo motor 2 and the Z-direction servo motor 22 all belong to the same type of servo motors and are all provided with a corresponding motor driver and a corresponding encoder, and a control program reads the encoder to obtain control information for controlling the motion of the servo motor, and drives the servo motor to control the motion of the roller brush 3 by the motor driver. The motion control information comprises a motion speed, a torque and the like of the servo motor.

The connecting block 29 at each part is provided with reverse threads which are engaged with the threads of the vertical lead screw 25 or the horizontal lead screw 21 connected to the connecting block, and the servo motor drives the lead screw to rotate so as to drive the connecting block 29 to move in the vertical direction or the horizontal direction. Two connecting blocks 29 are connected to each vertical lead screw 25 and each horizontal lead screw 21, and the threads of the two connecting blocks 29 are arranged in opposite directions, so that when the lead screws rotate, the motion directions of the two connecting blocks 29 are just opposite, or the two connecting blocks move oppositely, or move reversely. The movable block 30 is a passive component, and is driven by the connecting block 29 through the transmission of the vertical lead screw 25 or the roller brush 3 to move, and moves correspondingly and consistently with the connecting block 29 on the slide rail. The fixing block 31 is an intermediate connecting member between the connecting block 29 or the movable block 30 and the vertical lead screw 25 or the roller brush 3.

The self-rotating motor axially arranged at the front end of the roller brush 3 executes the instruction of the control program to control the rotation of the roller brush 3. A first pressure sensor 26 is arranged at the end part of the output shaft of the self-rotating motor and monitors the rotation resistance of the roller brush 3 and feeds back information to a control program, and the control program of the self-rotating motor preferentially calls motor motion control information corresponding to the feedback information of the first pressure sensor 26.

The Z-direction servo motor 22 arranged at the upper end of the vertical lead screw 25 executes the instruction of the control program to control the vertical motion of the roller brush 3. A second pressure sensor 14 arranged at the end part of the output shaft of the Z-direction servo motor 22 monitors the motion resistance of the roller brush 3 and feeds back the information to the control program, and the control program of the Z-direction servo motor 22 preferentially calls the motor motion control information corresponding to the feedback information of the second pressure sensor 14.

The Y-direction servo motor 2 arranged at the left side of the horizontal lead screw 21 executes the instruction of the control program to drive the horizontal motion of the roller brush 3. A third pressure sensor 15 is arranged at the end part of the output shaft of the Y-direction servo motor 2, and the third pressure sensor 15 monitors the motion resistance of the roller brush 3 and feeds back the information to the control program.

The infrared photoelectric sensors 27 are arranged on the side panels 32 on two sides of the rack 5, and the infrared photoelectric sensors 27 monitor the moving position of the pet and feed back information to the control program. The control program of the Y-direction servo motor 2 preferentially calls the motor motion control information corresponding to the feedback information of the third pressure sensor 15 and the infrared photoelectric sensors 27.

Specifically, the water outlet mechanism comprises: a water storage device 6, an electric heating element 4, a water mist spray head 41, a storage box 1, a pressure pump 7, a peristaltic pump, a pipeline assembly 10 and a mesh plate 11.

The water storage device 6 is used to store water for cleaning;

the water stored in the water storage device 6 is heated by the heating part and kept at a certain temperature, and the electric heating element 4 is arranged in the water storage device 6;

the water mist spray heads 41 are arranged on inner side walls, an inner lower wall and an inner top wall of the rack 5, and the water for cleaning is converted into high-pressure fine water mist for cleaning the pet by the water mist spray heads 41 to rinse the body of the pet without any dead angle;

the storage box 1 is connected to the water storage device 6 by the pipeline assembly 10, the storage box 1 is used to place a shower gel and/or a deodorant, a peristaltic pump is arranged at the outlet end of the storage box 1, the outflow volume of the shower gel and/or the deodorant is accurately controlled by the peristaltic pump, the shower gel and/or the deodorant flows down from the pipeline under the action of gravity or by the peristaltic pump, and the shower gel and/or the deodorant merges with water in the water storage device 6 at a connection of the pipeline and enters the pipeline to produce a mixed liquid;

the mixed liquid or the water for cleaning, after being pressurized by the pressure pump 7, flows into the roller brush 3 through the pipeline to spray the mist liquid; and the mesh plate 11 filters the cleaning wastewater, and the cleaning wastewater is discharged by a water collecting tray 12 arranged at the lower part and a drainage device at the bottom of the water collecting tray.

A plurality of storage boxes 1 are provided and loaded with different shower gels, and one of the storage boxes 1 can be loaded with a deodorant. A solenoid valve switch is provided at the outlet of the storage box 1, and the solenoid valve switch can be controlled based on a program setting.

Specifically, the pressure pump 7 is connected to a water outlet pipe of a water heater and an outlet end of the shower gel, and is pressurized by the pressure pump 7 and then pumped into a pipeline of the cleaning system.

In a specific embodiment, the drying mechanism comprises: an electric heating element 4, an infrared photoelectric sensor 27, a temperature sensor 28, an inlet fan 8 and an air supply fan 9.

Figure 11:
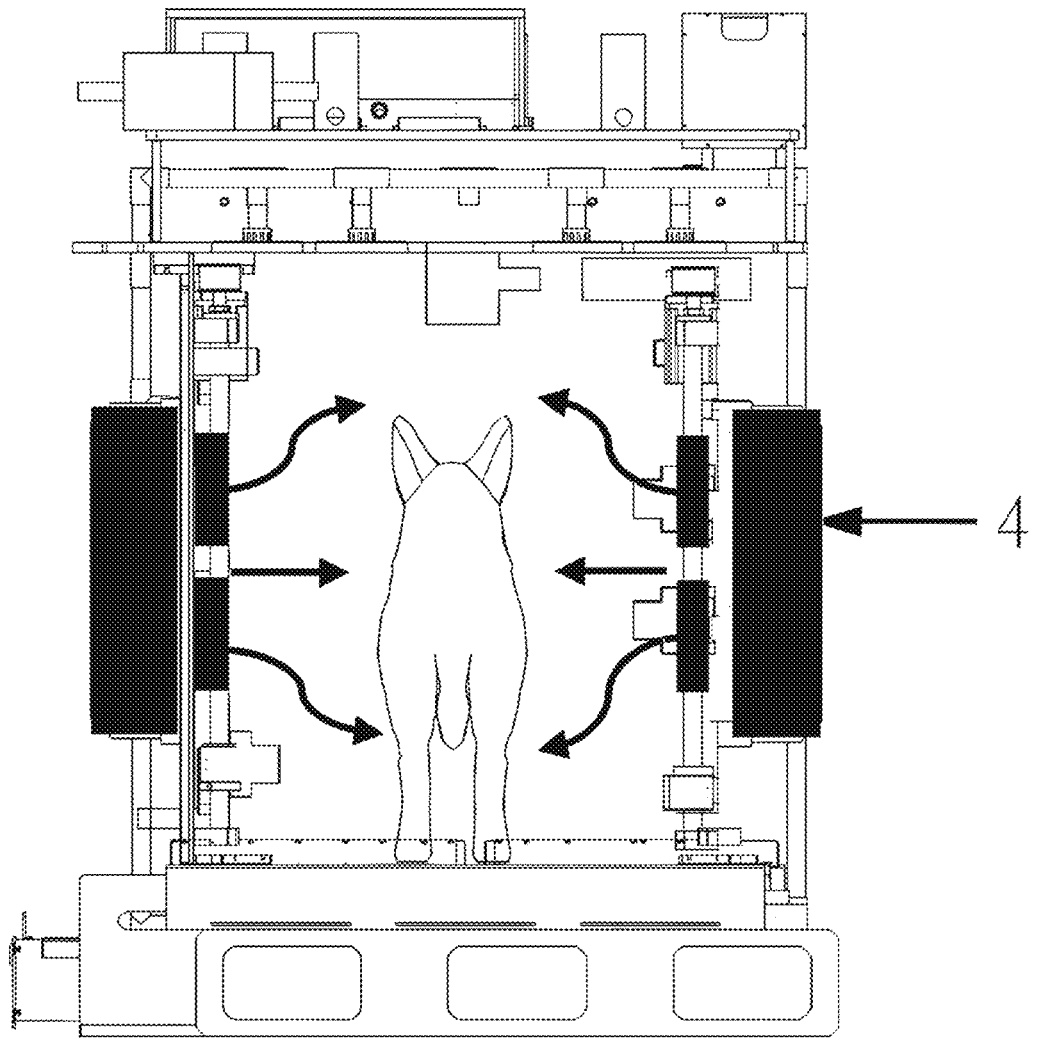
FIG. 11 is a partial schematic diagram of hot air blowing of a drying mechanism.

Referring to FIG. 11, two heating elements 4 are arranged on the main sheet metal wall panels on the left and right side surfaces of the automatic pet cleaning equipment, and the two heating elements 4 are respectively arranged at the middle of the two ends of the main sheet metal wall, for a total of 4 heating elements 4.

At the left and right side surfaces of the automatic pet cleaning equipment, 6 fans are evenly arranged in the middle of the main sheet metal wall, for a total of 12 fans. After the cleaning processes 1, 2 and 3 are completed, the fans which are symmetrically distributed in the middle of the main sheet metal walls at the two sides are firstly turned to slowly start an exhaust system, discharge water vapor, and prepare for the hot air.

Following the above steps, after the fans have run for 3 s, the four heating devices shown above are started simultaneously to ensure that the overall ambient temperature in the drying device is less than 32° C. (about 90° F.) to prevent the pet from feeling uncomfortable (when the temperature approaches 35° C. (about 95° F.), the pet begins to feel uncomfortable, may have a stress reaction, and even may suffer from heatstroke).

At the left and right side surfaces of the automatic pet cleaning equipment, 3 infrared light sensors are evenly arranged on the main sheet metal wall close to the positions near the fans, which can detect the temperature and the movement of the pet. The interior of the cleaning equipment is completely in the detection range of the sensors, and the infrared radiation change of an object can be captured, therefore, the real-time detection and feedback can be performed when the temperature changes.

Figure 10:
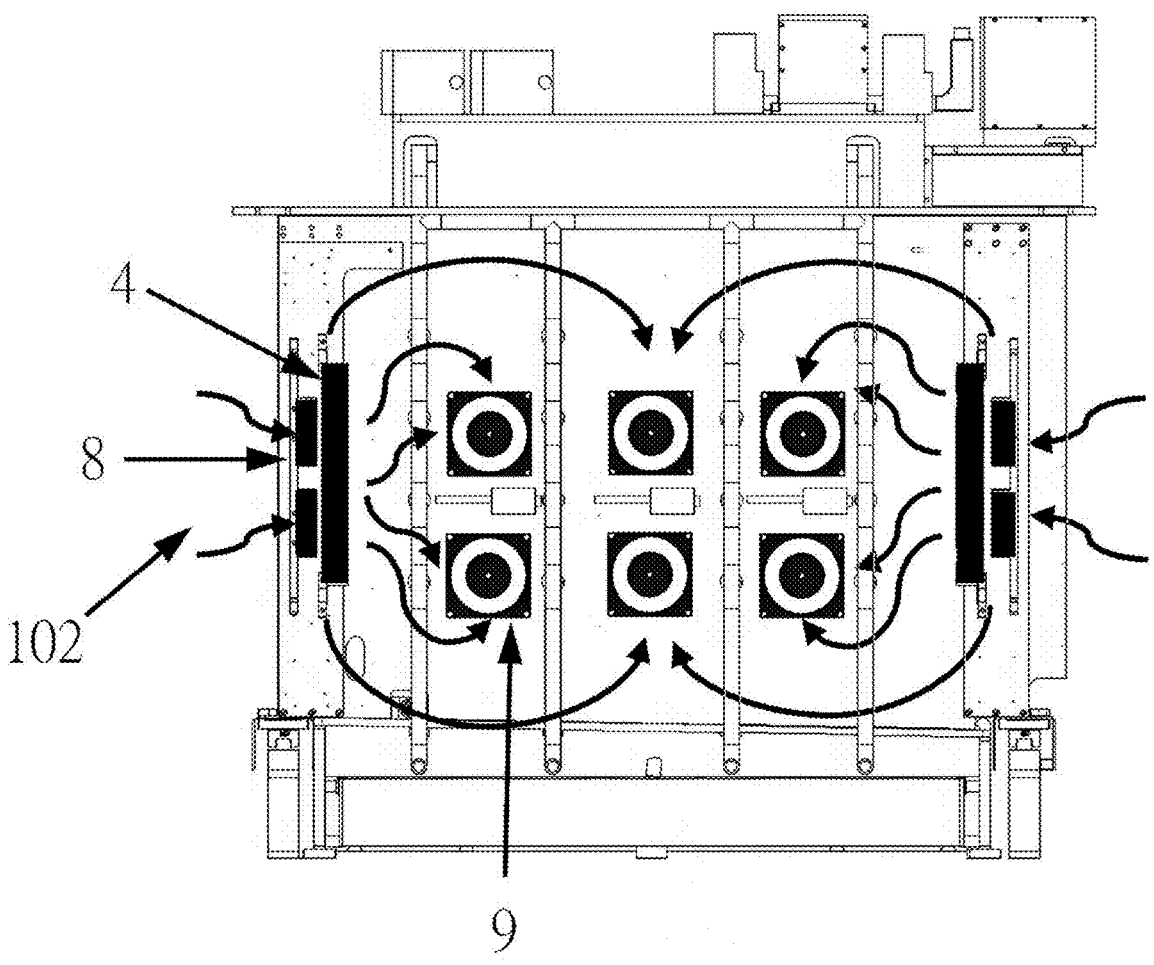
FIG. 10 is a partial schematic diagram of air intake and air supply of a drying mechanism.

Specifically, FIG. 10 shows a wall panel heating surface provided by the present invention, the air inlets and the hot air outlets in this area are shown, the room temperature air 102 enters from two sides shown by 102, and the hot air is heated by the heating element 4 and then supplied from the middle air supply fan 9, wherein the inlet fan 8 is an inlet fan of an outdoor room temperature air 102, and the air supply fan 9 is a hot air outlet fan arranged at the hot air outlet. The heating element 4 is adjacent to two inlet fans 8, and the room temperature or outdoor room temperature air 102 of the air source is heated and then discharged along with 6 groups of air supply fans 9 evenly arranged.

Figure 12:
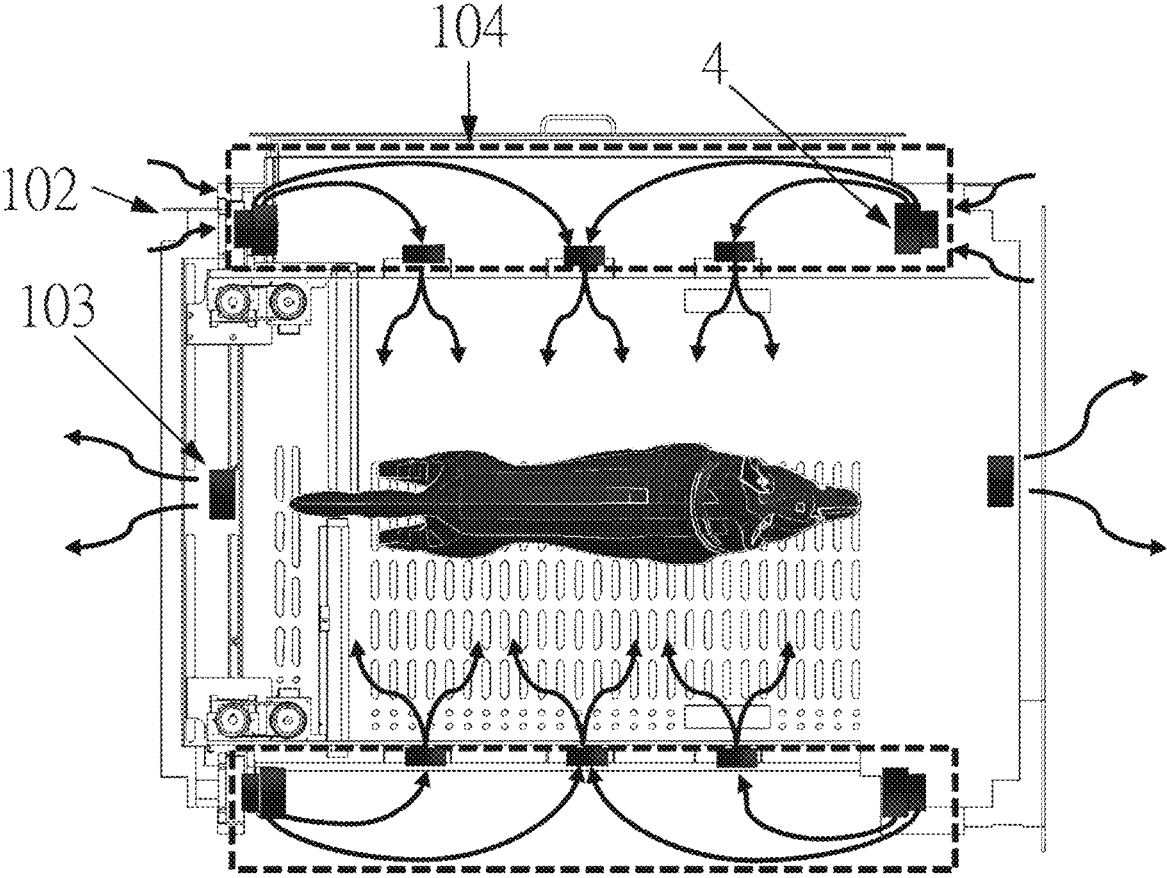
FIG. 12 is a top view of an air blowing path of a drying mechanism.

FIG. 12 is a top view of air conveying of the drying mechanism according to this embodiment. The room temperature air is supplied to the equipment from the outside, and since the internal area of the equipment forms a box-like closed space 104, the cold air passing through the heating element 4 is heated and then conveyed to the pet cleaning space by the internal fan, and the heated air dries the cleaned pet in three-dimensional manner from two sides and then is discharged by the outlet fans 103 arranged at the inlet and the outlet.

Specifically, two adjacent surfaces of the two moving seats of the rack 5 are respectively provided with a bathing inlet and a bathing outlet, and an inner side of the top of the rack 5 is provided with an ultraviolet lamp through which disinfection is performed.

Specifically, the water mist spray head 41 can spray pressurized water onto the pet in different modes, i.e., in a mist or column form. The direction and intensity of the spray head can be adjusted based on the pet size and the cleaning part. Generally, the terminal spraying pressure should be 0.2 Mpa to 0.8 Mpa.

Figure 8:
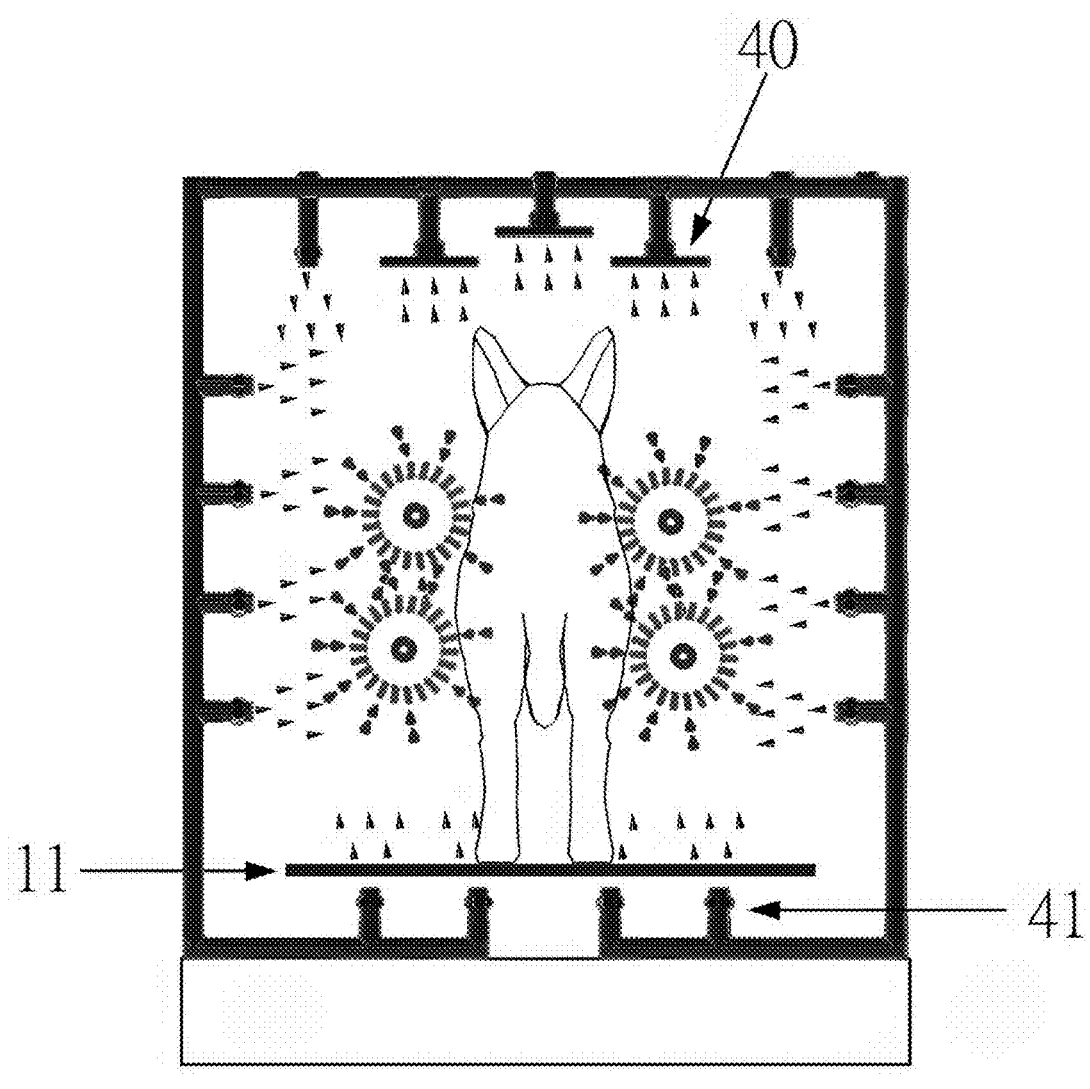
FIG. 8 is a schematic diagram of spraying of a cleaning terminal.

More specifically, the full-automatic pet cleaning machine of the present invention provides a top spray design similar to a human shower room, and the top shower head can evenly spray water downwards at the top of the full-automatic pet cleaning machine to simulate natural rainfall, so that the pet cleaning machine helps the pet relax and evenly covers the whole body of the pet, is particularly suitable for the pet who is first exposed to the automatic pet cleaning machine for automatically cleaning, and reduces the sense of pressure. Specifically, the water mist spray head 41 is arranged at the bottom of the rack 5 of the full-automatic pet cleaning machine, and the water mist spray head 41 and the side spray head can spray fine water mist suitable for pet cleaning, so that the bottom of the pet body can be cleaned without any dead angle. The impact of the water mist should not make the pet feel panic and discomfort. According to the experimental data, small and medium pressure values are used, and the pressure value reference range is 0.1 Mpa to 0.5 Mpa (about 2-5 kg/cm3). The water outlet pressure value should be moderate, and the spraying should be gentle. A top spray head 40 is arranged at the top of the rack 5 of the full-automatic pet cleaning machine, water is sprayed from the top of the spray head, and the arrangement of the bottom and side spray heads is shown in FIG. 8.

Specifically, the water storage device 6 is used to store water for cleaning.

Specifically, the water outlet mechanism further comprises a heating part, and the water stored in the water storage device 6 is heated by the heating part and kept at a certain temperature.

In a specific embodiment, specifically, the water storage device 6 and the heating part can be replaced by a water heater. The water heater is mainly a storage water heater and can also be an instant water heater, which is arranged at the top of the equipment and is a main container for storing the water for cleaning for the full-automatic pet cleaning machine. The water heater has a certain capacity to meet at least one or more cleaning demands. The water filling is automatically controlled by a solenoid valve. The water stored in the water heater is heated in advance by the heating system, and the temperature is maintained not less than 45° C. in summer and not less than 55° C. in winter to ensure that there is enough warm water during water discharging.

Specifically, the storage box 1 is provided at the top of the rack 5 and is connected to the water storage device 6 by the pipeline, the storage box 1 is used to place a shower gel and/or deodorant, a peristaltic pump is arranged at the outlet end of the storage box 1, the outflow volume of the shower gel and/or the deodorant is accurately controlled by the peristaltic pump, the shower gel and/or the deodorant flows down from the pipeline under the action of gravity or by the peristaltic pump, and the shower gel and/or the deodorant merges with water in the water storage device 6 at a connection of the pipeline and enters the pipeline to produce a mixed liquid.

Specifically, the full-automatic pet cleaning machine further comprises a pressure pump 7, and the mixed liquid or the water for cleaning, after being pressurized by the pressure pump 7, flows into the roller brush 3 through the pipeline to spray the mist liquid.

The pressure pump 7 pressurizes the water in the water tank and delivers the pressurized water to the cleaning spray head or shower head. By increasing the water pressure, the water flow is more powerful, which helps to remove dirt and grease on the pet hair. The pressurized pressure should be 0.1 Mpa to 0.75 Mpa.

Specifically, the full-automatic pet cleaning machine further comprises a hot air blowing dry part, and the hair is dried by the hot air blowing dry part.

Figure 9:
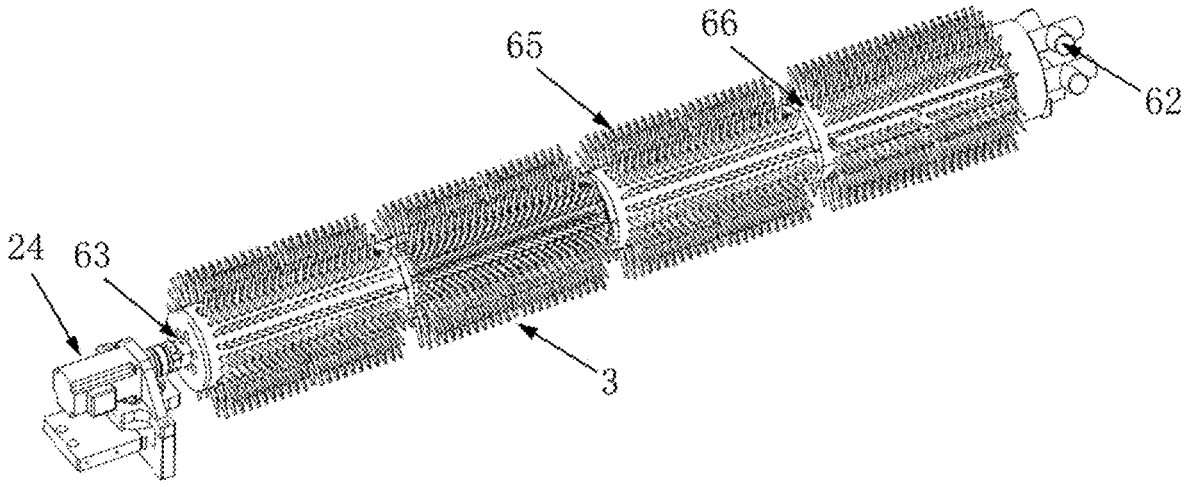
FIG. 9 is a schematic diagram of a roller assembly.

In a specific embodiment, referring to FIG. 9, the roller brush 3 comprises:

a roller 63, antenna fixing blocks 66, an antenna 65 and a water-air interface 62;

the antenna fixing blocks 66 are circumferentially arranged on an outer wall of the roller 63, the antenna fixing blocks 66 are semicircular cylinders, a hollow support cylinder is formed by the antenna fixing blocks 66, and the water-air interface 62 is formed in the support cylinder, and the water-air interface 62 is used to pass water and gas; and the antenna 65 is a hollow conical cylinder that is up-and-down communicated and has a step at the bottom end, and the antenna 65 is used to spray water or detergent foam in a cleaning stage and to blow hot air in a drying stage through the end part.

Specifically, the roller brush 3 contains a rolling brush, an antenna fixing block 66, an antenna 65 and a water-air interface 62. The roller brush 3 is provided with a servo motor in the axial direction to provide with rotational power. The roller brush 3 is also provided with a first pressure sensor 26 at the end part of the servo motor, which can conveniently sense the pressure. If the hair entanglement and too large motor resistance occur, the pressure sensor can sense and stop to ensure the safety of the pet. The equipment is provided with four self-rotating motors totally, the motors are all servo motors and are provided with drivers, and the drivers are controlled by a central control module unit to perform the motion control of the cleaning rolling brush.

Specifically, two Z-direction servo motors 22, one Y-direction servo motor 2, four roller brushes 3 (including a first roller brush, a second roller brush, a third roller brush and a fourth roller brush) and corresponding four self-rotating motors are arranged, the motors are all servo motors and are provided with drivers, and the drivers are controlled by a central control module unit to perform the motion control of the cleaning rolling brush.

Figure 4:
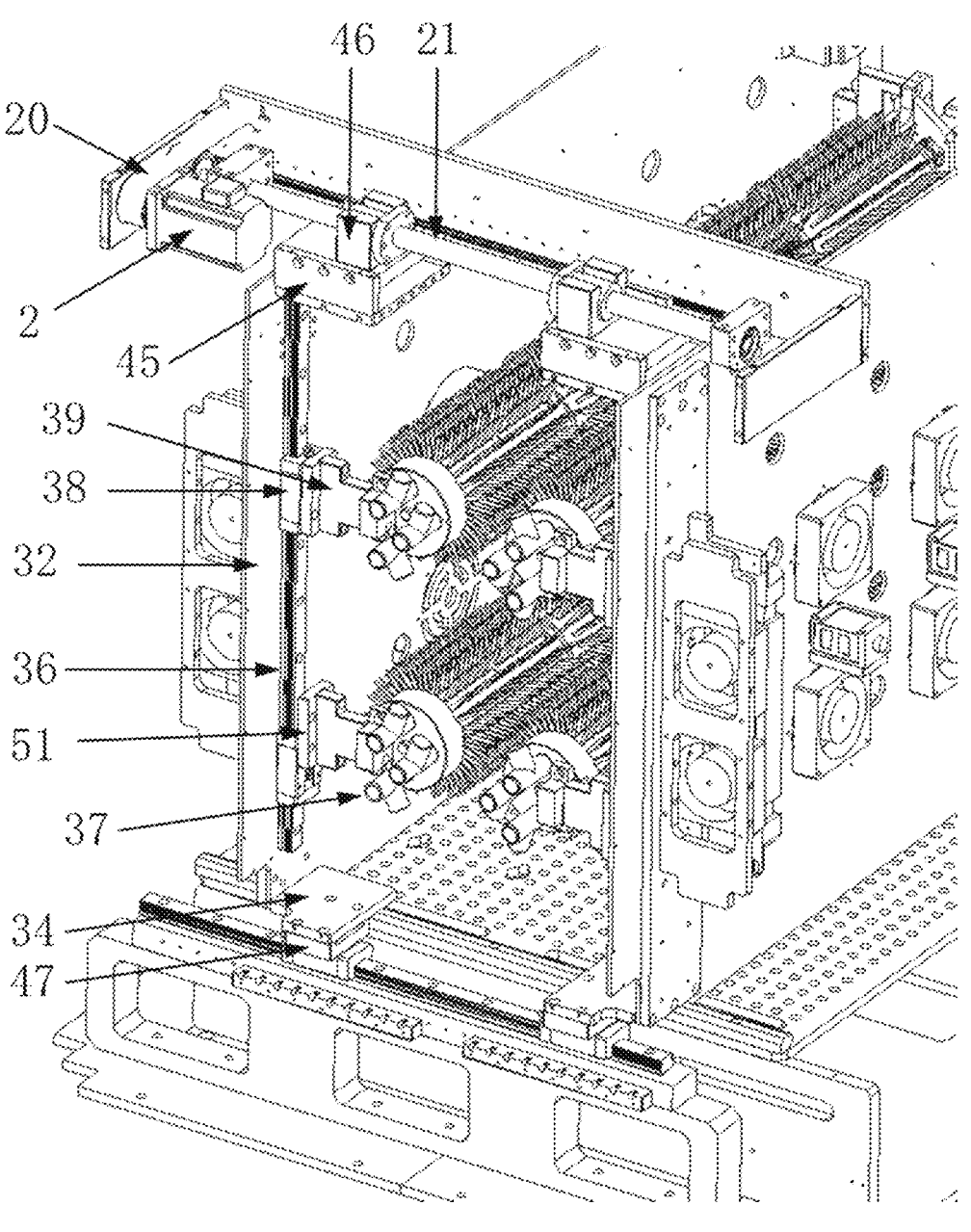
FIG. 4 is a connection diagram of pipeline side assemblies of a roller mechanism assembly.

Specifically, as shown in FIG. 4, the mechanism of the roller brush 3 is provided with a water pipe joint 37, the water pipe can pass through the shower liquid mixed with water at the front end, and hot air for drying can be allowed to pass through after the cleaning is completed. The connecting block 29 of the rolling brush mechanism is connected to the movable block 30, the slider connecting block 51 and the slider fixing block 39 on the vertical slide rail 36, the vertical slide rail 36 is connected to the side panel 32, the side panel 32 is connected to the bottom fixing block 34, and the bottom fixing block 34 is connected to the sliding parts on the horizontal slide rail 35, so that when the connecting plate at the bottom of the part 34 moves, all the parts on the connecting plate, including the side panel 32, the lead screw, the servo motor, the roller brush 3 assembly, the electric heating element, the fan and the like, move along with the connecting plate.

Figure 3:
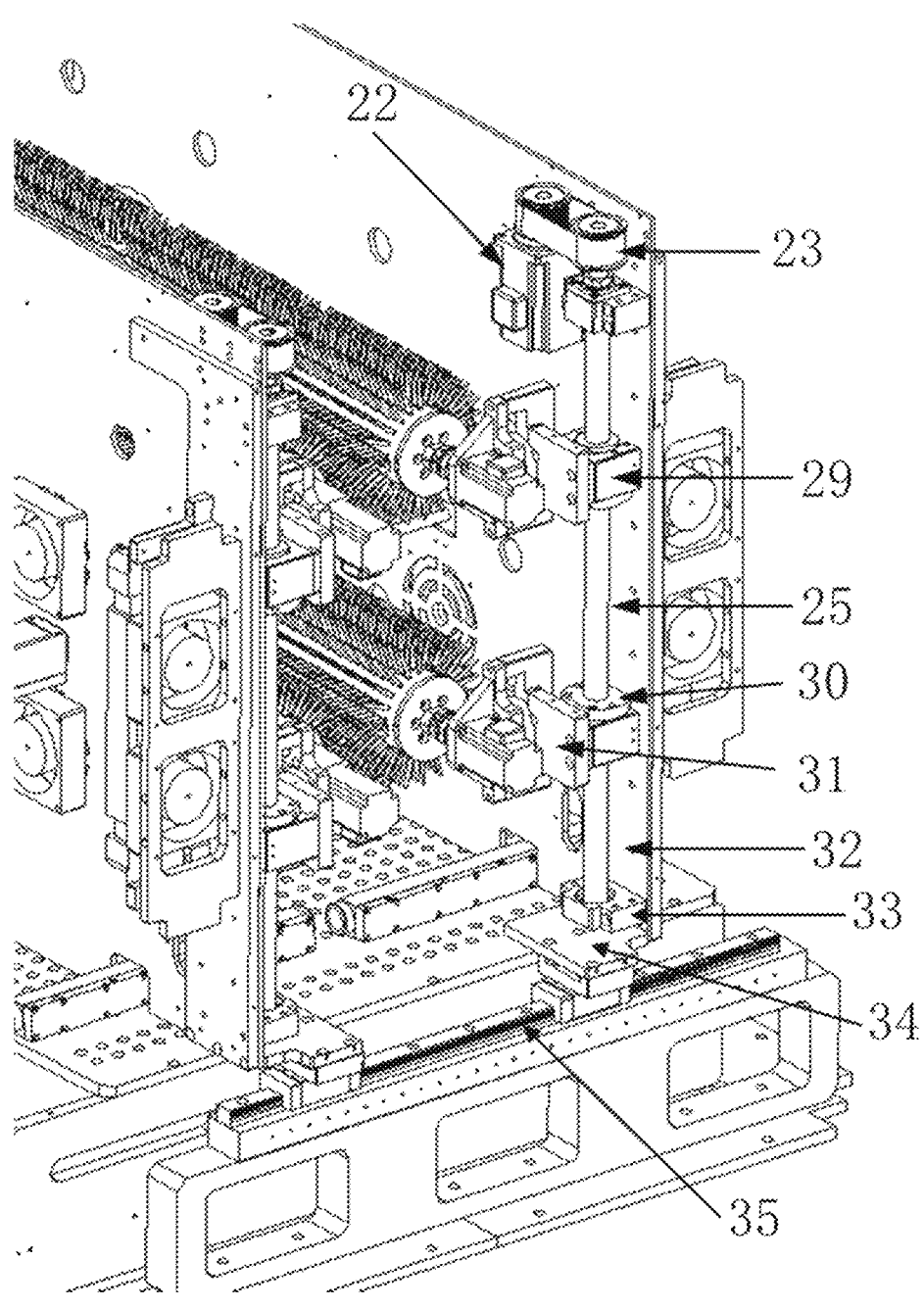
FIG. 3 is a connection diagram of side assemblies of a motor of a roller mechanism.

Specifically, as shown in FIG. 3, the first roller brush and the second roller brush are connected to the fixing block 31, the fixing block 31 is connected to the connecting block 29, and the two connecting blocks 29 positioned at the upper and lower positions are provided with threads in opposite directions, so that when the Z-direction servo motor 22 moves, the two connecting blocks 29 positioned at the upper and lower positions simultaneously move in different directions, thereby achieving the purpose of cleaning the pet up and down and massaging the pet to a certain extent.

Figure 5:
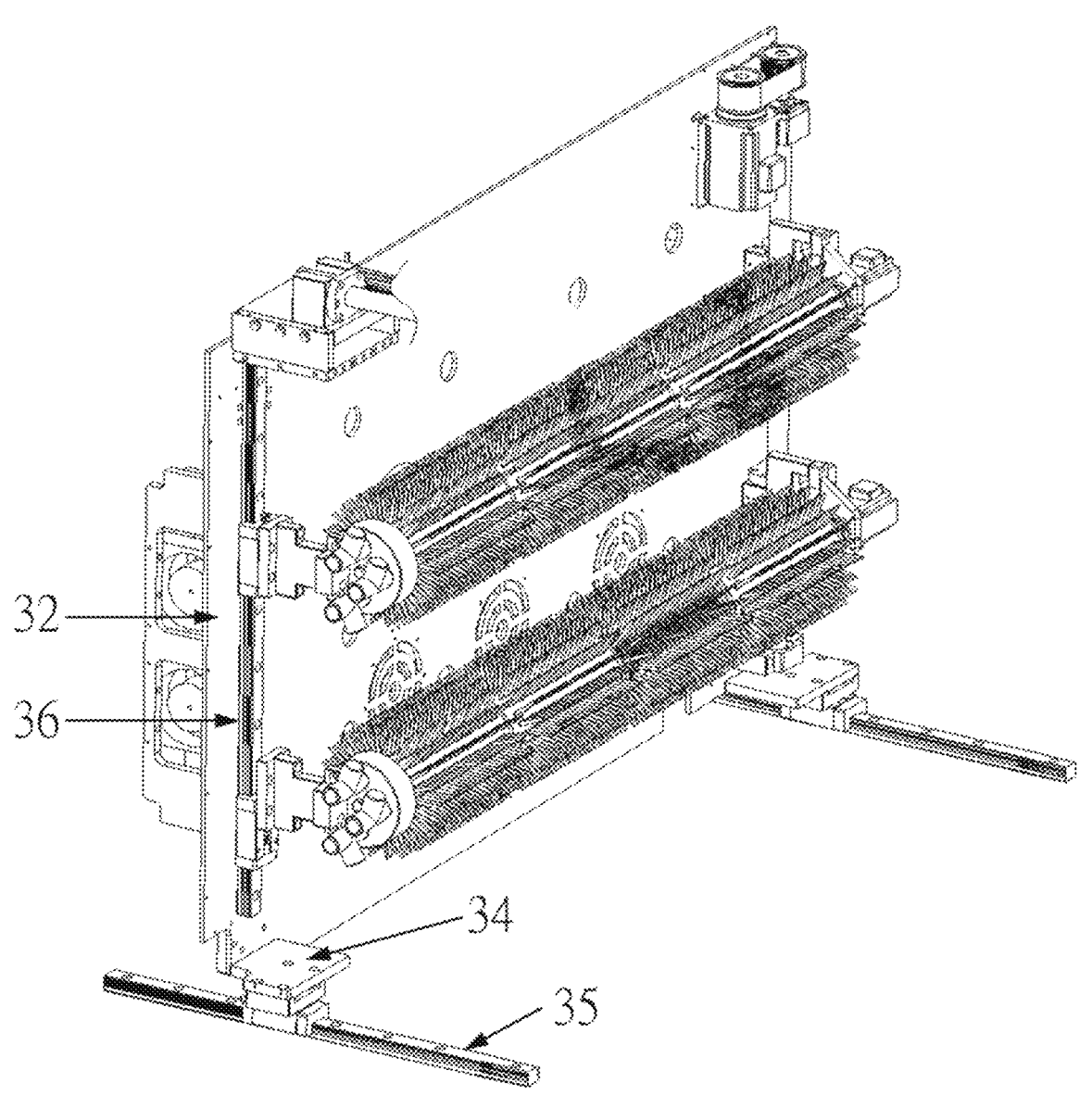
FIG. 5 is a schematic diagram of the assembly of a roller mechanism assembly moving in the Y direction.

Specifically, as shown in FIG. 5, a Y-direction servo motor 2 is arranged, the motor drives the lead screw to drive two roller groups simultaneously, and the motor can also drive two roller groups to move in the opposite direction, so that the rollers are close to or far away from the pet. When the Y-direction servo motor 2 moves, the motor drives the lead screw to move, and drives all parts above the horizontal slide rail 35 as a whole and another group of mechanisms relatively to move toward the center, namely, the two groups of mechanisms move relatively.

Specifically, two groups of Z-direction servo motors 22 are provided, as shown in FIG. 3, to respectively control two different groups of roller brushes 3. The Z-direction servo motor 22 controls the reciprocating motion of the roller brush 3 in the Z direction, the Z-direction servo motor 22 is connected to the lead screw through the second belt pulley mechanism 23, an upper connecting block 29 and a lower connecting block 29 which are connected to the lead screw are arranged, and the threads of the upper connecting block and the lower connecting block are arranged in opposite directions, so that the upper and lower roller brushes 3 are driven to move towards the center, namely, the two groups of roller brushes 3 move relatively.

Specifically, the self-rotating motor controlling self-rotation motion of the corresponding roller brush 3 based on feedback information of the corresponding first pressure sensor 26 comprises:

$$\omega_i \begin{cases} 0.5 \cdot \omega_{max}, & P_i < P_{low} \\ \omega_{max}, & P_{low} \le P_i \le P_{mid} \\ \omega_{max}\left(1 - \dfrac{P_i - P_{mid}}{P_{high} - P_{mid}}\right), & P_{mid} \le P_i \le P_{high} \\ 0, & P_i > P_{high} \end{cases}$$

wherein $\omega_i$ represents a motion parameter value controlled by an $i^{th}$ self-rotating motor, $P_i$ represents information of an $i^{th}$ first pressure sensor 26, $P_{low}$ represents a set low pressure value, $P_{mid}$ represents a set medium pressure value, and $P_{high}$ represents a set high pressure value.

Specifically, P is a set basic pressure value, P=9.8 Kpa. $P_{low}$ represents a set low pressure value, $P_{low}$=P.

$P_{mid}$ represents a set medium pressure value, $P_{mid}$=a*P, and a is an adjustable constant weighting coefficient.

$P_{high}$ represents a set high pressure value, $P_{high}$=2a*P.

The Z-direction servo motor 22 controlling the vertical lead screw 25 to rotate based on feedback information of the corresponding second pressure sensor 14 to drive the roller brush 3 to move vertically comprises:

$$\omega_j \begin{cases} A, & P_j < P_{j,low} \\ 0, & P_{j,low} \le P_k \le P_{j,high} \\ -A, & P_j > P_{j,high} \end{cases}$$

wherein $\omega_j$ represents a rotation speed parameter value of the Z-direction servo motor 22 at the position j, the motor rotates forwardly when $\omega_j$ is a positive number, two roller brushes 3 connected to the vertical lead screw 25 move in a vertical direction close to each other, the motor rotates reversely when $\omega_j$ is a negative number, two roller brushes 3 connected to the vertical lead screw 25 move in a vertical direction away from each other, and A is a constant and represents a normal rotation speed value of the Z-direction servo motor 22. $P_j$ represents a pressure value of the second pressure sensor 14 of the Z-direction servo motor 22 at j, $P_{j,low}$ represents a low pressure value set at j, and $P_{j,high}$ represents a high pressure value set at j.

The Y-direction servo motor 2 controlling the horizontal lead screw 21 to rotate based on feedback information of the corresponding third pressure sensor 15 to drive the roller brush 3 to move horizontally comprises:

$$\omega_k \begin{cases} B, & P_k < P_{k,mid} \\ 0, & P_{k,mid} \le P_k \le P_{k,high} \\ -B, & P_k > P_{k,high} \end{cases}$$

wherein $\omega_k$ represents a rotation speed parameter value of the Y-direction servo motor 2 at k, the motor rotates forwardly when $\omega_k$ is a positive number, the roller brushes 3 of the two moving seats connected to the horizontal lead screw 21 move towards a horizontal direction close to each other, the motor rotates reversely when $\omega_k$ is a negative number, the roller brushes 3 of the two moving seats connected to the horizontal lead screw 21 move towards a horizontal direction away from each other, B is a constant and represents a first rotation speed value of the Y-direction servo motor 2, $P_k$ represents an instantaneous pressure value of the third pressure sensor 15 at k where the Y-direction servo motor 2 is positioned, $P_{k,mid}$ represents a medium pressure value set at k, and $P_{k,high}$ represents a high pressure value set at k.

A side panel 32 of the rack 5 is provided with an infrared photoelectric sensor 27, which monitors position information of the pet and feeds back the information to the Y-direction servo motor 2, and the Y-direction servo motor 2 controlling the horizontal lead screw 21 to rotate based on feedback information of the corresponding second pressure sensor 14 and the feedback information of the infrared photoelectric sensor 27 to drive the roller brush 3 to move horizontally comprises:

$$\omega_k \begin{cases} C, & d_k > d_{high} \\ 0, & d_{mid} \le d_k \le d_{high} \\ -C, & d_k < d_{mid} \end{cases}$$

wherein $\omega_k$ represents a rotation speed parameter value of the Y-direction servo motor 2 at k, the motor rotates forwardly when $\omega_k$ is a positive number, the roller brushes 3 of the two moving seats connected to the horizontal lead screw 21 move towards a horizontal direction close to each other, the motor rotates reversely when $\omega_k$ is a negative number, the roller brushes 3 of the two moving seats connected to the horizontal lead screw 21 move towards a horizontal direction away from each other, C is a constant and represents a second rotation speed value of the Y-direction servo motor 2, $d_k$ represents an instantaneous distance value of the infrared photoelectric sensor 27 of the Y-direction servo motor 2 at k, $d_{mid}$ represents an upper limit value of a safe distance set at k, and $d_{high}$ represents a maximum distance value set at k.

Specifically, the upper limit of the safe distance may be set to 10 cm, and the maximum distance may be set to 30 cm, both of which are adaptively adjusted based on the pet size.

Specifically, the control program of the Y-direction servo motor 2 receives the feedback information of the third pressure sensor 15 and the infrared photoelectric sensor 27 simultaneously and generates a corresponding control instruction. A control instruction for moving the roller brushes 3 away from each other is higher than an instruction for keeping the roller brushes 3 in position, and the position keeping instruction is higher than a control instruction for moving the rollers closer to each other.

Specifically, the inlet fan 8 and the air supply fan 9 of the drying mechanism are driven by servo motors. The servo motor executes the instruction of the control program to move. The temperature sensor 28 monitors the temperature inside the drying mechanism and feeds back information to the control program. A control logic is set up as follows:

$$\omega(T) \begin{cases} \omega_{max}, & T \le T_{high} \\ \omega_{max}\left(1 - \dfrac{T - T_{high}}{T_{safe} - T_{high}}\right), & T_{mid} < T < T_{safe} \\ 0, & T \ge T_{safe} \end{cases}$$

wherein $\omega(T)$ represents a rotation speed parameter value of a servo motor when the temperature sensor 28 displays temperature T, T represents a displayed temperature value of the temperature sensor 28, $T_{safe}$ represents an upper limit of a safety temperature inside equipment and is set to 35° C., and $T_{high}$ represents a high temperature mark value inside the equipment and is set to 30° C.

Specifically, four groups of roller brushes 3 are provided. To ensure the safety of pet in the cleaning process, the motion of the four groups of roller brushes 3 is designed as follows:

1. smooth start and stop;
2. adaptive speed control design, the rotating speed of the motor is automatically adjusted according to the pet size, the hair type and the pet reaction, and the rotating speed is slower for large or long-haired pet and slightly faster for small or short-haired pets;
3. sensor feedback, a force feedback sensor is provided at the motor, and an infrared photoelectric sensor 27 is provided inside to monitor the position and activity of the pet in real time; if the pet is detected to move abnormally or overreact, the motor will stop or slow down immediately.
4. safety locking, if the door of the full-automatic pet cleaning machine is opened or the pet is detected to try to escape, all the motors stop moving immediately until the safety is confirmed and then are restarted; and
5. immediate stop button: in any situation that may pose a danger to the pet, anyone can stop the power immediately to rescue the pet.

Figure 6:
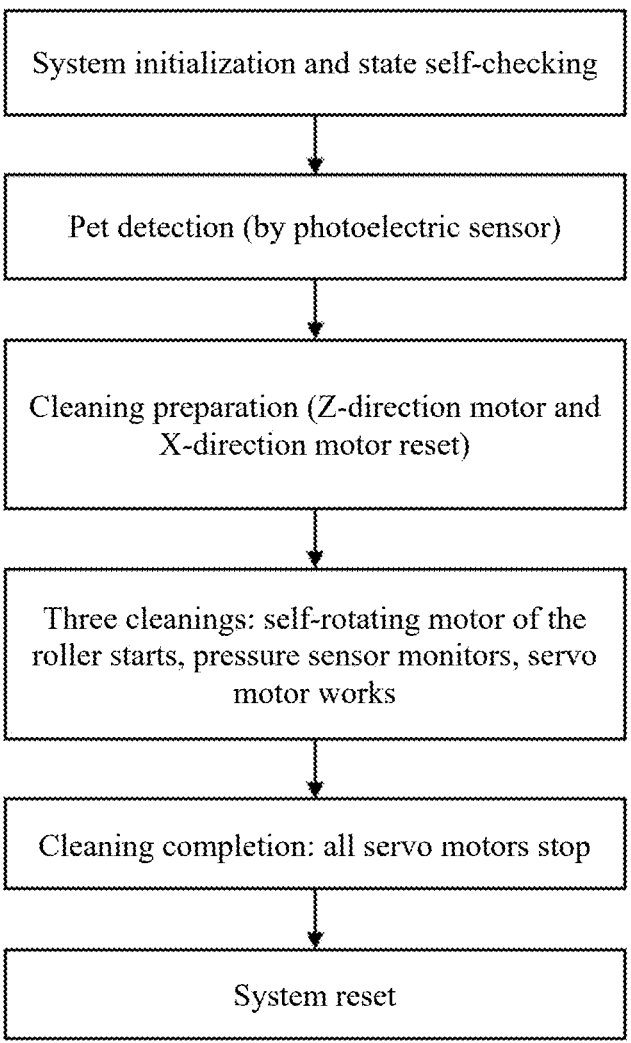
FIG. 6 is a schematic diagram of a working process of a roller mechanism.

More specifically, refer to the main working process of the roller brushes 3 during cleaning shown in FIG. 6.

Power-on initialization: a power supply of the full-automatic pet cleaning machine is started, and a self-checking servo motor of an electric system is initialized; the connection and the state of the Z-direction and Y-direction motors and the self-rotating motor are detected and confirmed to be good; and pre-cleaning parameters, such as the rotating speed of the roller, the moving speed in the Y direction and the Z direction and other parameters (adjusted by the touch screen) are preset.

Pet loading: a door of the full-automatic pet cleaning machine is opened, and the user places the pet into a safety fixing device inside the roller; a sensor is used to detect whether the pet has been placed correctly; the door is closed and a door locking mechanism is activated to ensure safety and sealing.

Roller operation: the self-rotating motor is started to slowly rotate to simulate manual kneading action, so that water flow can contact the whole body of the pet; the Y-direction servo motor 2 and the Z-direction servo motor 22 are in motion, the roller is precisely controlled by the Y-direction servo motor 2 and the Z-direction servo motor 22 to reciprocate along the axial direction based on a cleaning requirement, and the moving speed and the moving direction can be changed to adapt to the cleaning process at different stages.

Figure 7:
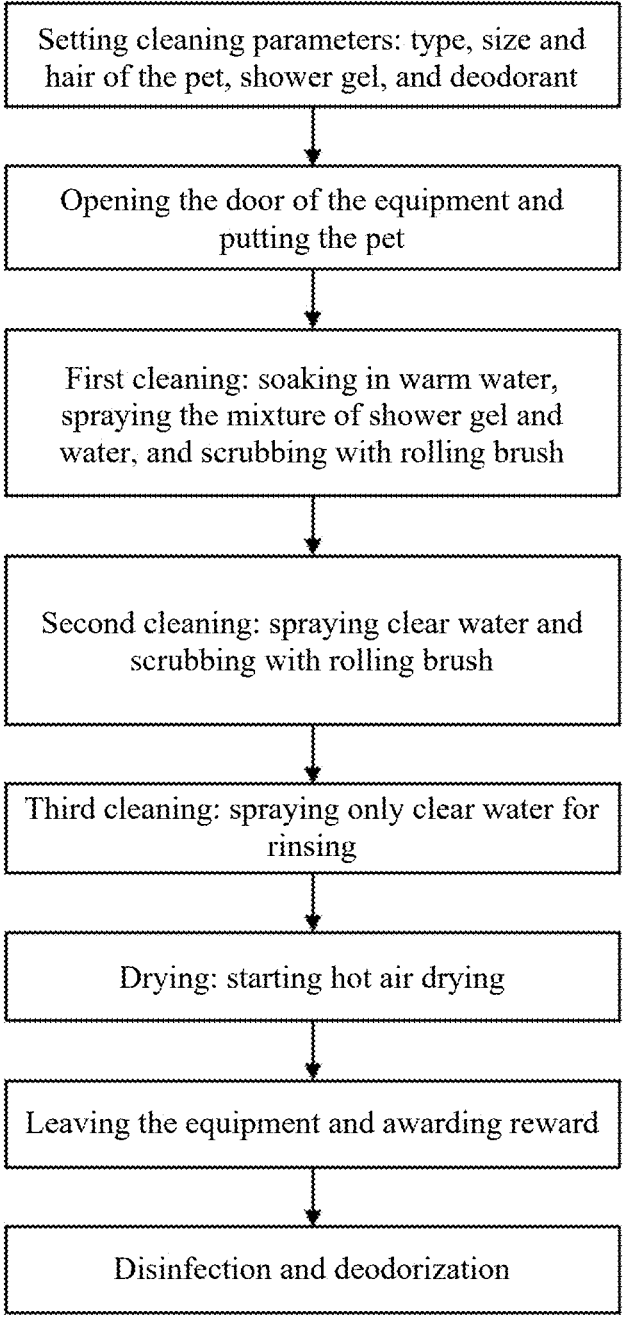
FIG. 7 is a basic process of pet cleaning.

Referring to FIG. 7, this embodiment further discloses a control method of a full-automatic pet cleaning machine that is the full-automatic pet cleaning machine described in the above embodiment, which comprises the following steps:

step I: adjusting parameters based on a pet type, a pet physique and a hair type;

step II: opening a bathing door, and closing the bathing door after a pet enters the cleaning machine;

step III: performing warm water spraying on four sides by a heating system and the pressure pump 7 to moisten the hair and the skin of the pet; controlling a shower gel to be released from the storage box 1, delivered to the water mist spray head 41 through the pipeline and then sprayed after mixing with the water for cleaning; controlling the self-rotation of the roller brush 3, the horizontal motion of the roller brush 3, and the vertical motion of the roller brush 3 to scrub the pet;

step IV: closing a switch of the storage box 1 for placing the shower gel, continuously spraying clear water to remove shower gel residues, and scrubbing the pet through the self-rotation of the roller brush 3, the horizontal motion of the roller brush 3, and the vertical motion of the roller brush 3;

step V: returning the roller brush 3 to an original position, and rinsing the pet by using clear water through the water mist spray head 41;

step VI: drying the hair of the pet through a hot air blowing dry part;

step VII: after the cleaning is completed, opening the bathroom door; and step VIII: sterilizing with the ultraviolet lamp, and releasing deodorant for deodorization.

Specifically, the step III and the step IV are a first cleaning and a second cleaning. In the cleaning process, warm water and cleaning liquid supply systems are started, water and shower gel are sprayed into the roller by the spray head, the roller rotates and moves towards Z and Y directions, and meanwhile, the water flow fully contacts the hair and skin of the pet, so that stains are removed; and a wastewater collection system works synchronously, discharges the cleaned wastewater and introduces a fresh water source.

The step V is a third cleaning, i.e., rinsing. After the main cleaning is completed, the rinsing mode is switched, and clean water rinses the pet by the roller again; the drying system is started immediately after rinsing, and the roller continues to rotate to help the water evaporate; and the self-rotating motor can adjust the speed based on a drying requirement at this stage to promote the fluffy and drying of the pet hair.

After the cleaning is completed, the servo motor is stopped, and the roller brush 3 stops rotating; the full-automatic pet cleaning machine sends a completion signal, the door is opened, and the pet is taken out; and the full-automatic pet cleaning machine stands by and prepares for the next round of cleaning.

Specifically, one shower gel storage box 1 and one deodorant storage box 1 are arranged at the top of the full-automatic pet cleaning machine and are connected to the arranged pipeline and water system, a peristaltic pump is arranged at the outlet end of the storage box 1 and accurately controls the outflow of the shower gel or the deodorant, the deodorant and the shower gel in the storage boxes 1 flow down from the pipeline due to gravity or the action of the peristaltic pump, merge with water at a connection of the pipeline and enter the pipeline, and the produced mixed liquid is pressurized by the pressure pump 7 and flows into a flexible rolling brush head at the tail end of the roller brush 3 through the pipeline to spray the mist liquid for the first cleaning, and the cleaning time is kept to be not less than 5 min for ensuring the cleaning effect;

before the second cleaning, after the control valve switches arranged at the outlets of the shower gel and deodorant storage boxes 1 are closed, only warm water from the water system directly enters the pipeline, is pressurized by the pressure pump 7 and then flows into a flexible rolling brush head at the tail end of the roller brush 3 through the pipeline to spray mist liquid for the second cleaning, and the cleaning time is kept to be not less than 3.5 min for ensuring the cleaning effect; and during the third cleaning, the roller is reset, the valves at the outlet ends of the shower gel storage box 1 and the deodorant storage box 1 are closed, and only clean water is used to rinse the pet.

In another aspect, this embodiment further discloses a control system of a full-automatic pet cleaning machine that is the full-automatic pet cleaning machine described in the above embodiment, which comprises:

a main control module, a touch screen parameter setting module, a sensor module, a servo-driven control module and a water system control module;

the main control module controls and manages the full-automatic pet cleaning machine;

the sensor module monitors the state information of the equipment and the pet in real time, including feedback pressure values and temperature value parameters, and comprises pressure sensors (including a second pressure sensor 14, a third pressure sensor 15 and a first pressure sensor 26), a temperature sensor 28 and an infrared photoelectric sensor 27;

the servo-driven control module is controlled by the main control module to drive the servo motor to move in the Y and Z directions, so that the accurate motion of the related assemblies of the Y-direction and Z-direction servo motors 22 is achieved, and the servo motor assembly comprises a servo motor driver, a motor body, and an encoder;

the main control module controls the driver to drive the servo motor to move so as to achieve the rotary motion of the self-rotating motor, and the servo motor assembly comprises a servo motor driver, a motor body and an encoder; and the water system control module controls storage, distribution and release of the cleaning liquid, and ensures that the cleaning liquid is used reasonably based on the size and hair type of the pet.

The water system control module comprises: a first cleaning unit, a second cleaning unit and a third cleaning unit;

the first cleaning unit controls the heating system and the pressure pump 7 to spray warm water on four sides to moisten the hair and skin of the pet; controls the shower gel to be released from the storage box 1, delivered to the water mist spray head 41 through the pipeline and then sprayed after mixing with the water for cleaning; and controls the self-rotation of the roller brush 3, the horizontal motion of the roller brush 3, and the vertical motion of the roller brush 3 to scrub the pet;

the second cleaning unit controls to close a switch of a storage box for placing a shower gel 1, continuously sprays clear water to remove shower gel residues, controls the self-rotation of the roller brush 3, the horizontal motion of the roller brush 3 and the vertical motion of the roller brush 3 to scrub the pet; and the third cleaning unit controls the roller brush 3 to return to the original position, and rinses the pet by using clear water through the water mist spray head 41.

The embodiments in the specification are all described in a progressive manner, and each embodiment focuses on differences from other embodiments, and portions that are the same and similar between the embodiments may be referred to each other. Since the apparatus disclosed in the embodiment corresponds to the method disclosed in the embodiment, the description is relatively simple, and reference may be made to the partial description of the method.

The above description of the disclosed embodiments enables those skilled in the art to implement or use the present invention. Various modifications to these embodiments will be readily apparent to those skilled in the art, and the generic principles defined herein may be applied to other embodiments without departing from the spirit or scope of the present invention. Thus, the present invention is not intended to be limited to these embodiments shown herein but is to be accorded the broadest scope consistent with the principles and novel features disclosed herein.

The invention claimed is:

1. A full-automatic pet cleaning machine, comprising: a bathing mechanism and a drying mechanism, wherein the bathing mechanism is configured to clean a pet, and the drying mechanism is configured to dry hair of the pet;

the bathing mechanism comprises: a water outlet mechanism and a cleaning terminal mechanism connected to the water outlet mechanism;

the cleaning terminal mechanism comprises: a rack, a horizontal lead screw, a vertical lead screw, a vertical slide rail, a self-rotating motor, a Y-direction servo motor, a Z-direction servo motor and roller brushes;

two groups of roller brushes are symmetrically arranged along two moving seats of the rack, each group of roller brushes comprises two roller brushes, each roller brush is rotatably mounted on a corresponding mounting seat, one end of each roller brush is provided with one self-rotating motor, an end part of an output shaft of the self-rotating motor is provided with a corresponding pressure sensor, and the self-rotating motor controls self-rotation motion of the corresponding roller brush based on feedback information of the corresponding pressure sensor;

a first side of each group of roller brushes is connected to the vertical lead screw, a second side of each group of roller brushes is connected to the vertical slide rail, one end of the vertical lead screw is provided with the Z-direction servo motor, an end part of an output shaft of the Z-direction servo motor is provided with a corresponding pressure sensor, and the Z-direction servo motor controls the vertical lead screw to rotate based on feedback information of the corresponding pressure sensor to drive the roller brush to move vertically; and the horizontal lead screw is rotatably mounted at a top of the rack, two ends of the horizontal lead screw are in threaded connection with the two moving seats, respectively, an end part of an output shaft of the Y-direction servo motor is provided with a corresponding pressure sensor, and the Y-direction servo motor controls the horizontal lead screw to rotate based on feedback information of the corresponding pressure sensor to drive the roller brush to move horizontally.

2. The full-automatic pet cleaning machine according to claim 1, wherein the roller brush comprises:

a roller, antenna fixing blocks, antennas and a water-air interface;

the antenna fixing blocks are circumferentially arranged on an outer wall of the roller and are semicircular cylinders, a hollow support cylinder is formed by the two antenna fixing blocks, and the water-air interface is formed in the hollow support cylinder and is configured to pass water and gas; and the antennas are hollow conical cylinders that are up-and-down communicated, each of the antennas is fixed in a mounting groove of the antenna fixing block by an end step structure and forms a hollow connection with the hollow support cylinder, and the antenna is configured to spray water or detergent foam in a cleaning stage and to blow hot air in a drying stage.

3. The full-automatic pet cleaning machine according to claim 1, wherein the roller brush is connected to a fixing block, the fixing block is connected to a connecting block, the connecting block is provided with reverse threads engaged with threads of the vertical lead screw, and the connecting block is driven by the Z-direction servo motor to move vertically.

4. The full-automatic pet cleaning machine according to claim 1, wherein the self-rotating motor controlling the self-rotation motion of the corresponding roller brush based on the feedback information of the corresponding pressure sensor comprises:

$$\omega_i \begin{cases} 0.5 \cdot \omega_{max}, & P_i < P_{low} \\ \omega_{max}, & P_{low} \le P_i \le P_{mid} \\ \omega_{max}\left(1 - \dfrac{P_i - P_{mid}}{P_{high} - P_{mid}}\right), & P_{mid} \le P_i \le P_{high} \\ 0, & P_i > P_{high} \end{cases}$$

wherein $\omega_i$ represents a motion parameter value controlled by an $i^{th}$ self-rotating motor, $P_i$ represents information of an $i^{th}$ pressure sensor, $P_{low}$ represents a set low pressure value, $P_{mid}$ represents a set medium pressure value, and $P_{high}$ represents a set high pressure value.

5. The full-automatic pet cleaning machine according to claim 1, wherein the Z-direction servo motor controlling the vertical lead screw to rotate based on the feedback information of the corresponding pressure sensor to drive the roller brush to move vertically comprises:

$$\omega_j \begin{cases} A, & P_j < P_{j,low} \\ 0, & P_{j,low} \le P_k \le P_{j,high} \\ -A, & P_j > P_{j,high} \end{cases}$$

wherein $\omega_j$ represents a rotation speed parameter value of the Z-direction servo motor at a position j, the Z-direction servo motor rotates forwardly when $\omega_j$ is a positive number, the two roller brushes connected to the vertical lead screw move in a vertical direction adjacent to each other, the Z-direction servo motor rotates reversely when $\omega_j$ is a negative number, the two roller brushes connected to the vertical lead screw move in a vertical direction away from each other, A is a constant and represents a normal rotation speed value of the Z-direction servo motor, $P_j$ represents a pressure value of the pressure sensor of the Z-direction servo motor at j, $P_{j,low}$ represents a low pressure value set at j, and $P_{j,high}$ represents a high pressure value set at j.

6. The full-automatic pet cleaning machine according to claim 1, wherein the Y-direction servo motor controlling the horizontal lead screw to rotate based on the feedback information of the corresponding pressure sensor to drive the roller brush to move horizontally comprises:

$$\omega_k \begin{cases} B, & P_k < P_{k,mid} \\ 0, & P_{k,mid} \le P_k \le P_{k,high} \\ -B, & P_k > P_{k,high} \end{cases}$$

wherein $\omega_k$ represents a rotation speed parameter value of the Y-direction servo motor at k, the Y-direction servo motor rotates forwardly when $\omega_k$ is a positive number, the roller brushes of the two moving seats connected to the horizontal lead screw move towards a horizontal direction adjacent to each other, the Y-direction servo motor rotates reversely when $\omega_k$ is a negative number, the roller brushes of the two moving seats connected to the horizontal lead screw move towards a horizontal direction away from each other, B is a constant and represents a first rotation speed value of the Y-direction servo motor, $P_k$ represents an instantaneous pressure value of the pressure sensor at k where the Y-direction servo motor is positioned, $P_{k,mid}$ represents a medium pressure value set at k, and $P_{k,high}$ represents a high pressure value set at k.

7. The full-automatic pet cleaning machine according to claim 1, wherein a side panel of the rack is provided with an infrared photoelectric sensor, the infrared photoelectric sensor monitors position information of the pet and feeds back the information to the Y-direction servo motor, and the Y-direction servo motor controlling the horizontal lead screw to rotate based on the feedback information of the corresponding pressure sensor or the information of the infrared photoelectric sensor to drive the roller brush to move horizontally comprises:

$$\omega_k \begin{cases} C, & d_k < d_{high} \\ 0, & d_{mid} \le d_k \le d_{high} \\ -C, & d_k > d_{mid} \end{cases}$$

wherein $\omega_k$ represents a rotation speed parameter value of the Y-direction servo motor at k, the Y-direction servo motor rotates forwardly when $\omega_k$ is a positive number, the roller brushes of the two moving seats connected to the horizontal lead screw move towards a horizontal direction adjacent to each other, the Y-direction servo motor rotates reversely when $\omega_k$ is a negative number, the roller brushes of the two moving seats connected to the horizontal lead screw move towards a horizontal direction away from each other, C is a constant and represents a second rotation speed value of the Y-direction servo motor, $d_k$ represents an instantaneous distance value of the infrared photoelectric sensor of the Y-direction servo motor at k, $d_{mid}$ represents an upper limit value of a safe distance set at k, and $d_{high}$ represents a maximum distance value set at k.

8. The full-automatic pet cleaning machine according to claim 1, wherein two adjacent surfaces of the two moving seats of the rack are respectively provided with a bathing inlet and a bathing outlet, and an inner side of the top of the rack is provided with an ultraviolet lamp, wherein disinfection is performed through the ultraviolet lamp.

9. The full-automatic pet cleaning machine according to claim 1, wherein the water outlet mechanism comprises: a water storage device, a heating part, a water mist spray head, a storage box, a pressure pump, a peristaltic pump, a pipeline assembly and a mesh plate;

the water storage device is configured to store water for cleaning;

the water stored in the water storage device is heated by the heating part and kept at a predetermined temperature;

a plurality of water mist spray heads are arranged on inner side walls, an inner lower wall and an inner top wall of the rack, and the water for cleaning is converted into fine water mist for cleaning the pet by the plurality of water mist spray heads to rinse a body of the pet;

the storage box is connected to the water storage device by the pipeline assembly, the peristaltic pump is arranged at an outlet end of the storage box, and cleaning liquid placed in the storage box flows out through the peristaltic pump and merges with the water in the water storage device at a connection of the pipeline assembly to enter a pipeline to produce a mixed liquid;

the mixed liquid or the water for cleaning, after being pressurized by the pressure pump, flows into the roller brush through the pipeline assembly to spray mist liquid; and the mesh plate discharges cleaning wastewater.

10. The full-automatic pet cleaning machine according to claim 1, wherein the drying mechanism comprises: an electric heating element, an inlet fan and an air supply fan;

after passing through the inlet fan, room temperature air is heated by the electric heating element and blown towards an inside of the rack by the air supply fan, and the hair of the pet is dried.

11. The full-automatic pet cleaning machine according to claim 1, wherein the drying mechanism further comprises: a temperature sensor, and a drying temperature is controlled based on feedback information of the temperature sensor, wherein a control logic is set up as follows:

$$\omega(T) \begin{cases} \omega_{max}, T \leq T_{high} \\ \omega_{max}\left(1 - \dfrac{T - T_{high}}{T_{safe} - T_{high}}\right), T_{mid} \leq T \leq T_{safe} \\ 0, T \geq T_{safe} \end{cases}$$

wherein $\omega(T)$ represents a rotation speed parameter value of a servo motor corresponding to the temperature T displayed by the temperature sensor at a predetermined moment, T represents a displayed temperature value of the temperature sensor at the predetermined moment, $T_{safe}$ represents an upper limit of a safety temperature inside equipment, and $T_{high}$ represents a high temperature mark value inside the equipment.

* * * * *